(12) United States Patent
Becker et al.

(10) Patent No.: US 6,331,176 B1
(45) Date of Patent: Dec. 18, 2001

(54) BLEED BACK CONTROL ASSEMBLY AND METHOD

(75) Inventors: Neil M. Becker, Temecula; Duncan Clarke, Murrieta; Chuck Peterson, Murrieta; Albert A. Quinones, Murrieta; Paul Haldeman, Murrieta; Kenneth K. Armstrong, Riverside; Victor Wilson, Quail Valley; Bruce Wilson, Escondido; Gary Thompson, Morgan Hill; William P. Colvan, San Diego, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/267,754

(22) Filed: Mar. 11, 1999

(51) Int. Cl.$^7$ ................................................. A61M 25/16
(52) U.S. Cl. ............................................. 604/533; 604/537
(58) Field of Search ................................ 604/533, 534, 604/535, 537, 538, 539, 284, 167, 246, 167.01–167.05

(56) References Cited

U.S. PATENT DOCUMENTS

| | | | |
|---|---|---|---|
| 4,341,239 | 7/1982 | Atkinson | 137/493 |
| 4,421,926 | 12/1983 | Stephens | 251/149 |
| 4,581,020 | 4/1986 | Mittleman | 604/175 |
| 4,610,469 | 9/1986 | Wolff-Mooij | 285/260 |
| 4,634,432 | 1/1987 | Kocak | 604/167 |
| 4,638,668 | 1/1987 | Leverberg et al. | 73/866.5 |
| 4,874,378 * | 10/1989 | Hillstead | 604/167 |
| 4,886,507 * | 12/1989 | Patton et al. | 604/284 |
| 4,935,010 | 6/1990 | Cox et al. | 604/122 |
| 4,960,412 | 10/1990 | Fink | 604/167 |
| 5,057,084 | 10/1991 | Ensminger et al. | 604/167 |
| 5,059,186 | 10/1991 | Yamamoto et al. | 604/280 |
| 5,064,416 | 11/1991 | Newgard et al. | 604/167 |

(List continued on next page.)

FOREIGN PATENT DOCUMENTS

| | | | | |
|---|---|---|---|---|
| 0 658 357 A2 | 6/1995 | (EP) | | A61M/39/06 |
| 0 875 262 A2 | 11/1998 | (EP) | | A61M/25/01 |

*Primary Examiner*—Richard K. Seidel
*Assistant Examiner*—Kevin C. Sirmons
(74) *Attorney, Agent, or Firm*—Fulwider Patton Lee & Utecht, LLP

(57) ABSTRACT

A bleed back control assembly and method for controlling blood loss during catheterization procedures includes a side arm body connected at the proximal end to a seal body. The side arm body comprises one or more branches, each having a lumen, and a finger rest on the exterior of at least one branch. The seal body comprises a cap assembly and a seal assembly. The seal assembly comprises a clamp seal and a bleed back seal, both made of elastomer and held by a seal holder. The cap assembly comprises a threaded cap and a funnel cap. The threaded cap is connected to the seal holder. Rotation of the threaded cap causes the clamp seal to open or close. The funnel cap comprises a dilator, and pressing the funnel cap causes the dilator to open an aperture in the bleed back control seal. A spring, wound around the dilator, returns the funnel cap to its original position, thus closing the bleed back seal. The bleed back seal self-sizes to devices introduced through its aperture. Dilating the bleed back control seal also allows purging of gases or fluids. The clamp seal can clamp a device introduced transluminally to maintain device position, and the clamp seal may also be closed to allow high pressure injections.

5 Claims, 15 Drawing Sheets

U.S. PATENT DOCUMENTS

| | | | |
|---|---|---|---|
| 5,085,645 | 2/1992 | Purdy et al. | 604/167 |
| 5,092,840 | 3/1992 | Healy | 604/83 |
| 5,106,054 | 4/1992 | Mollenauer et al. | 251/149 |
| 5,125,915 * | 6/1992 | Berry et al. | 604/283 |
| 5,147,336 * | 9/1992 | Wendell et al. | 604/283 |
| 5,195,980 | 3/1993 | Catlin | 604/167 |
| 5,269,764 | 12/1993 | Vetter et al. | 604/167 |
| 5,306,243 * | 4/1994 | Bonaldo | 604/86 |
| 5,324,271 | 6/1994 | Abiuso et al. | 604/167 |
| 5,338,314 * | 8/1994 | Ryan | 604/284 |
| 5,376,077 | 12/1994 | Gomringer | 604/167 |
| 5,382,230 | 1/1995 | Bonn | 604/32 |
| 5,458,640 * | 10/1995 | Gerrone | 604/264 |
| 5,474,536 * | 12/1995 | Bonaldo | 604/86 |
| 5,478,331 * | 12/1995 | Heflin et al. | 604/283 |
| 5,591,137 * | 1/1997 | Stevens | 604/296 |
| 5,599,305 * | 2/1997 | Hermann et al. | 604/95 |
| 5,599,327 * | 2/1997 | Sugahara et al. | 604/283 |
| 5,820,600 | 10/1998 | Carlson et al. | 604/167 |
| 5,911,710 * | 6/1999 | Barry et al. | 604/249 |

* cited by examiner

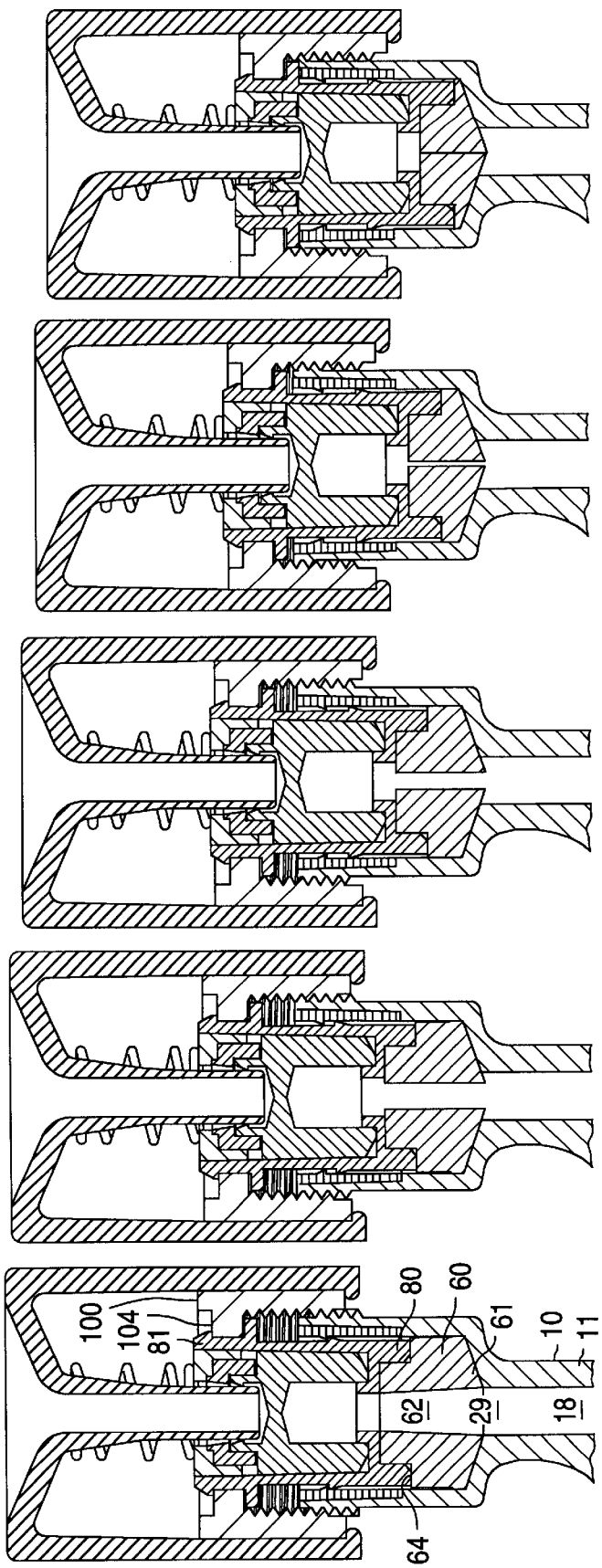

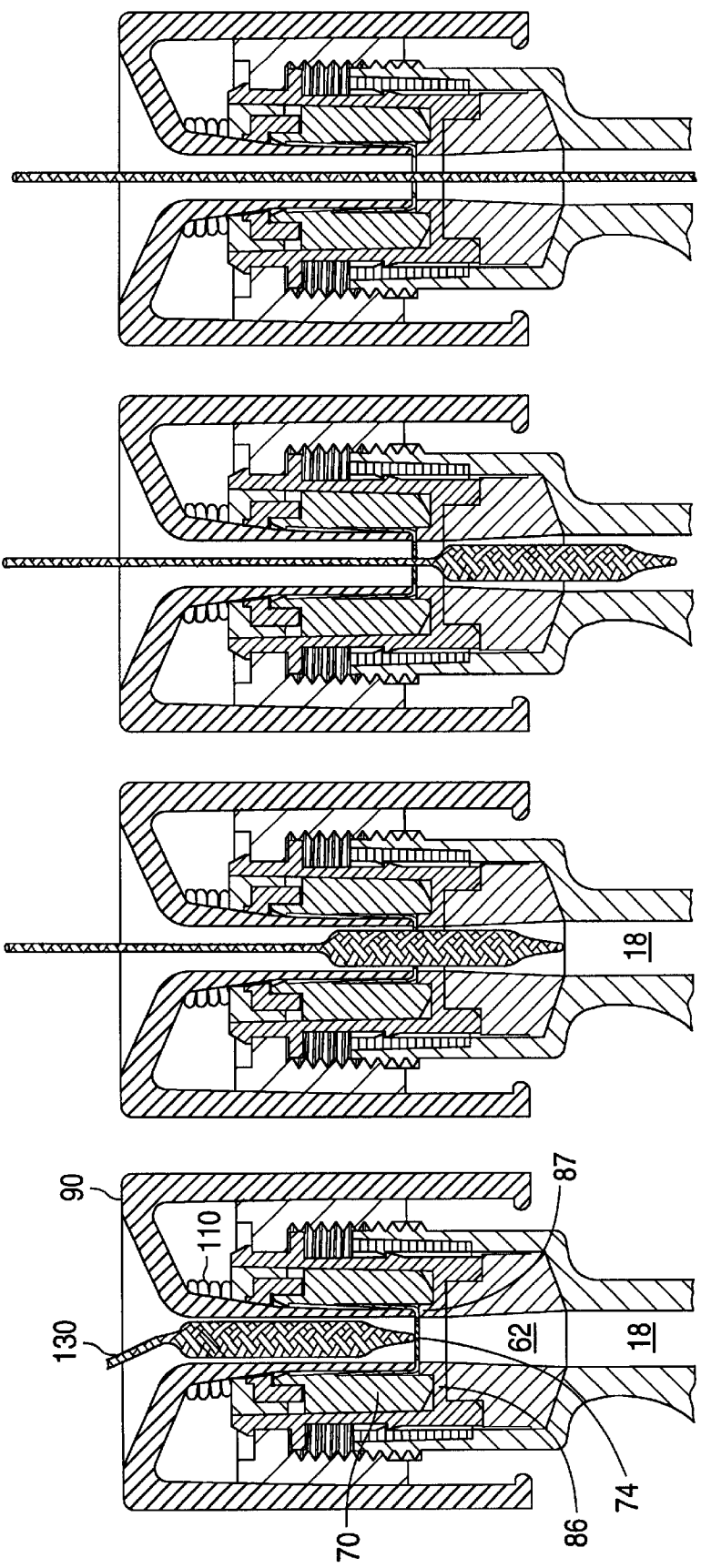

BLEED BACK CONTROL ASSEMBLY AND METHOD

BACKGROUND

This invention relates generally to a bleed back control assembly for controlling blood loss during vascular diagnostic or interventional procedures, such as insertion and removal of catheters from a patient's blood vessels.

Treatment of patients with diseases, such as coronary heart disease, can typically involve use of catheters, balloon catheters, stents, and other vascular intervention devices which are introduced transluminally, i.e. to and through the interior of a patient's blood vessels. Typically, catheterization procedures include the use of a hemostatic valve to reduce blood loss.

It is known in the art to provide a large bore rotating hemostasis valve (RHV) which attaches to the end of a guiding catheter and acts as an open/close valve. After a device is introduced into the lumen of an RHV, the RHV serves as a seal around the device to reduce blood loss. An RHV must be opened to allow introduction of an interventional device into the RHV's lumen, and must be closed to control blood loss while allowing device adjustment, such as moving it back and forth. A doctor must adjust a screw cap of a conventional RHV in order to adjust the seal around various devices introduced axially through the RHV's lumen. Conventional RHV's utilize a Touhy-Bourst seal design, which may be opened and closed by the user, but such a seal allows fluid to escape until properly adjusted.

A significant amount of the patient's blood may be lost during these adjustments of the RHV's screw cap which are required in order to move a device, such as a catheter, in and out of the RHV. When the RHV is not adjusted to seal around the device introduced in the RHV's lumen, there is no mechanism for inhibiting substantial bleed back or blood loss.

Accordingly, a conventional RHV allows excessive blood loss when the RHV is not adjusted or whenever the RHV is in the open position. This drawback in an RHV allows for excessive and undesirable blood loss from the patient. The excessive blood loss also creates a more ensanguined operating environment for the user of the RHV, increasing risks associated with unwanted exposure to blood (or other fluids) and making more difficult the manipulation or operation of devices.

For example, U.S. Pat. No. 5,269,764, issued to Vetter et al., discloses a hemostatic gasket and valve assembly, including a terminal plug, which can be rotated and thus tightened to cause radial compression of the hemostatic gasket.

SUMMARY

An advantage of the present invention is to provide a bleed back control assembly which permits diagnostic or interventional vascular procedures, such as insertion of devices like catheters, guide wires, or stent delivery systems in a patient's blood vessels, while controlling and significantly reducing the amount of blood loss, even when the catheter must be adjusted or moved.

Another advantage of the invention is to provide a bleed back control assembly which permits diagnostic or interventional vascular procedures, while allowing a user to clamp an interventional device introduced into the bleed back control assembly, to maintain device position while controlling blood loss.

A bleed back control apparatus in accordance with one aspect of the invention includes a side arm body having proximal and distal ends, and a seal body connected to the proximal end of the side arm body, where the seal mechanism includes a seal assembly and a cap assembly. The seal assembly comprises a bleed back control seal held within an interior chamber of a seal holder.

In another aspect, the cap assembly includes a threaded cap which is rotatably attached to the exterior of the proximal end of the side arm body and a funnel cap attached to the threaded cap.

In another aspect, a bleed back control seal in accordance with one aspect of the invention has a cylindrical body with a lumen, a web area covering a cross-section of the lumen and having a dilatable aperture, and the cylindrical body and web area are formed of an elastomer.

In another related aspect, the seal assembly further comprises a clamp seal with a cylindrical body tapering to a frustum, with a lumen through the cylindrical body and frustum, and the clamp seal is formed of an elastomer.

In another aspect, a side arm body in accordance with another aspect of the invention has a proximal end and means for sealing connected to the proximal end of the side arm body, where the means for sealing comprises means for controlling bleed back during use.

In a related aspect, a method in accordance with another aspect of the invention for controlling blood loss using a bleed back control assembly includes introducing a vascular intervention device (such as, but not limited to, a catheter) transluminally within the assembly, and forming a bleed back control seal around the introduced vascular intervention device.

Accordingly, with these and other apparatus and method aspects of the invention, a bleed back control assembly in accordance with one aspect of the present invention controls blood loss during insertion, movement, and removal of a vascular intervention device (such as catheter) from the assembly. The user can adjust a clamp seal to clamp a vascular intervention device introduced transluminally, such as a catheter, to maintain device position or perform high pressure injections. The user can also close the clamp seal, without a vascular intervention device introduced transluminally, to allow high pressure injections into the side arm body.

These and other aspects of the invention are described further below.

BRIEF DESCRIPTION OF THE DRAWINGS

FIGS. 11a to 11e are a cross-sectional view of an operation of a clamp seal in accordance with the present invention.

FIGS. 15a to 15d are a cross-sectional view of an insertion of a vascular intervention device (such as a catheter) through a dilated bleed back control seal in accordance with the present invention.

DETAILED DESCRIPTION

Referring to FIGS. 1a through 1d, the components of a bleed back control assembly 1 in accordance with one aspect of the invention are shown in relation one to the other.

Figure 1A:
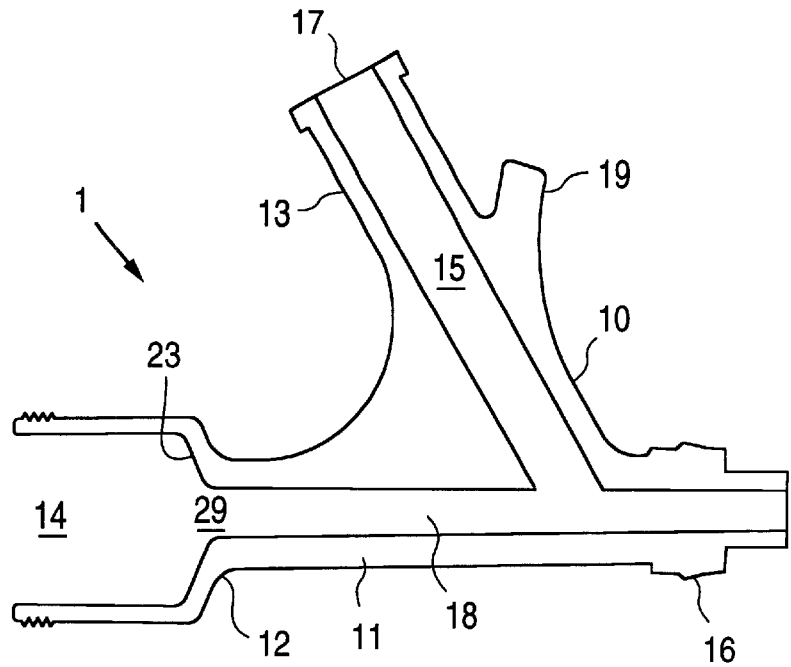
FIG. 1a is a cross-sectional view of a side arm body in accordance with the present invention.

Referring to FIG. 1a, a side arm body 10 has a proximal end 12 with a seal cavity 14 formed therein. Side arm body 10 also has a distal end 16. Side arm body 10 has a primary branch 11 and a secondary branch 13. A primary lumen 18 is formed through primary branch 11 of side arm body 10 and connects proximal end 12 to distal end 16. Side arm body 10 is thus a tube having a lumen allowing fluid (such as blood) to communicate from one end to the other. Fluid may also communicate between lumen 18 and seal cavity 14. A secondary lumen 15 is formed through secondary branch 13 of side arm body 10. Fluid may also communicate between lumen 18 of primary branch 11 and lumen 15 of secondary branch 13.

Figure 1B:
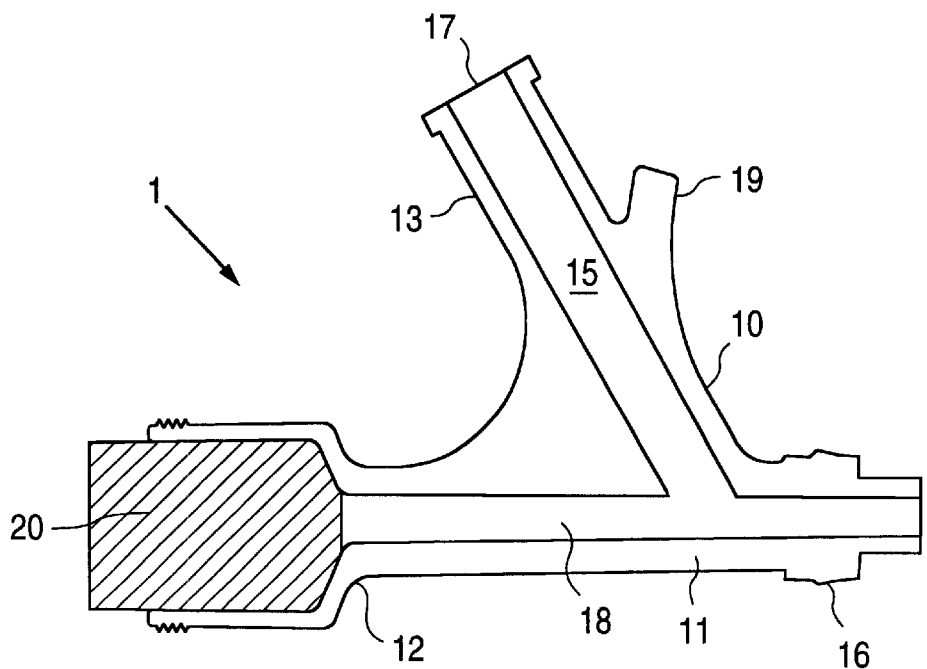
FIG. 1b is a cross-sectional view of a side arm body and seal assembly in accordance with the present invention.

Referring to FIG. 1b, a seal assembly 20 is held within seal cavity 14 at the proximal end 12 of side arm body 10. Seal assembly 20 is generally formed to conform to the shape and interior surface 23 of seal cavity 14. As discussed further below, seal assembly 20 comprises one or more seals made of elastic and resilient materials which may be readily deformed or stretched depending on user operation, and these seals will return to their original shape and position when released or disengaged.

Figure 1C:
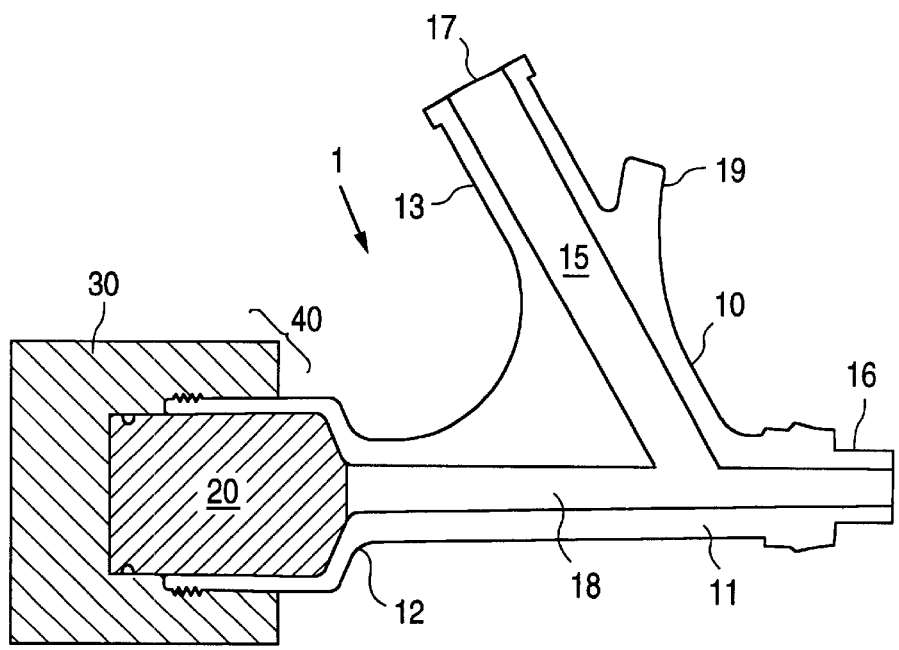
FIG. 1c is a cross-sectional view of a side arm body, a seal assembly, and a cap assembly in accordance with the present invention.

Referring to FIG. 1c, cap assembly 30 is connected to seal assembly 20 and is also connected to the exterior surface of seal cavity 14 at the proximal end 12 of side arm body 10. Cap assembly 30 contains seal assembly 20 within seal cavity 14 and, as described further below, allows user operation and adjustment of seal assembly 20. As described further below, the user may adjust seal assembly 20 to either open or close access to primary lumen 18 of side arm body 10, as well as clamp vascular intervention devices introduced into bleed back control assembly 1 to maintain device position or location. Seal body 40 comprises seal assembly 20 and cap assembly 30. As shown in FIG. 1c, a bleed back control assembly 1 in accordance with one aspect of the invention comprises side arm body 10 connected to seal body 40 at proximal end 12 of side arm body 10.

Figure 1D:
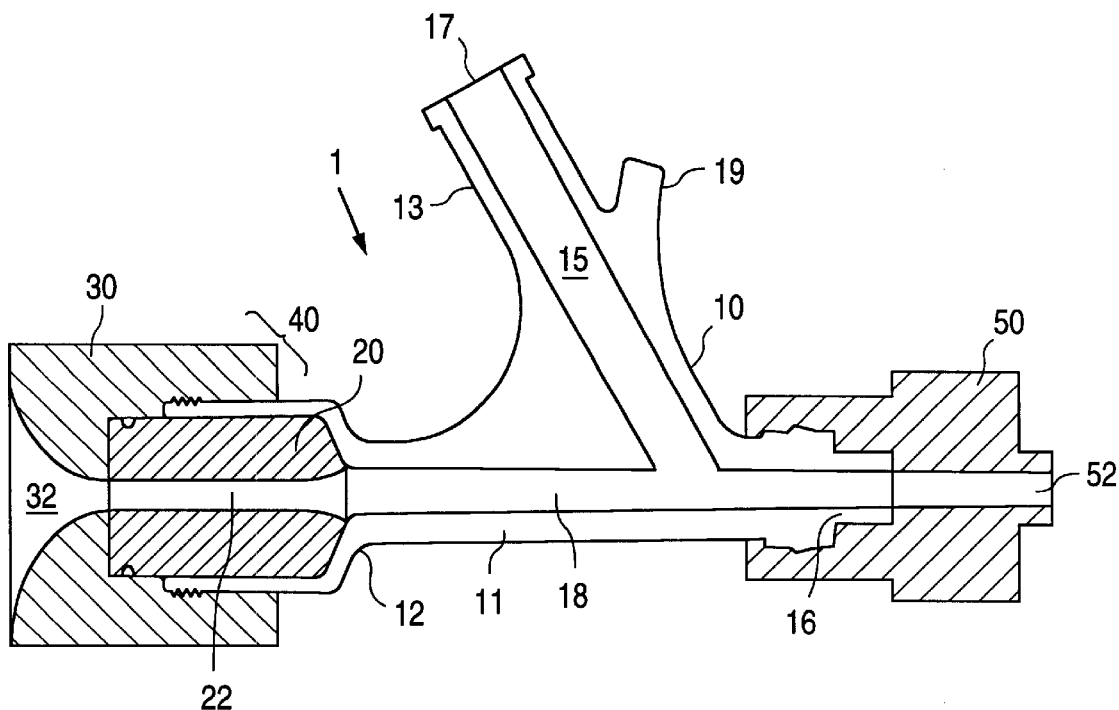
FIG. 1d is a cross-sectional view of a bleed back control assembly in accordance with the present invention.

Referring to FIG. 1d, another embodiment of bleed back control assembly 1 in accordance with the invention comprises side arm body 10 having a proximal end 12 and a distal end 16. A seal body 40, comprising seal assembly 20 connected to cap assembly 30, is attached to proximal end 12 of side arm body 10. Seal body 40 is a seal mechanism which includes one or more elastomeric seals and cap assembly 30 to retain these seals within seal cavity 14. Seal assembly 20 has an aperture 22 formed therethrough, and cap assembly 30 has an aperture 32 which is axially aligned with and proximal to seal assembly 20's aperture 22. Seal assembly 20's aperture 22 is also axially aligned with and proximal to primary lumen 18.

A male luer connector 50 which is 360 degrees rotatable is connected to distal end 16 of side arm body 10. Luer connector 50 has a lumen 52 which connects proximally with the distal end 16 of primary lumen 18 of side arm body 10.

In general, a user may operate bleed black control assembly 1 by inserting a vascular intervention device (such as a catheter) through aperture 32, then through aperture 22, into lumen 18, through lumen 52, and ultimately into a patient's body. A user may operate cap assembly 30 by either pressing, screwing, or unscrewing cap assembly 30. By operating cap assembly 30, a user may open or close seal assembly 20 and thereby either seal the connection between aperture 22 and lumen 18 or, when a vascular intervention device is introduced into bleed back control assembly 1, by clamping such a vascular intervention device by constricting a portion of aperture 22 of seal assembly 20. Because of seal assembly 20's elastomeric properties, seal assembly 20 provides control over blood loss during insertion and removal of vascular intervention devices through bleed back control assembly 1, as described further below.

Referring to FIGS. 1a to 10c, the structures of side arm body 10 and seal body 40 are shown. Side arm body 10 will be discussed first.

Side Arm Body

Referring to FIGS. 1a to 1d, 2, 4a, and 4b, side arm body 10 is substantially Y shaped and consists of a straight primary branch 11 and a secondary branch 13. Lumens 15 and 18 are formed within both the secondary branch 13 and primary branch 11, respectively.

Lumen 15 of secondary branch 13 provides access to, and is in fluid communication with, lumen 18 of primary branch 11. Secondary branch 13 can be used for, but is not limited to, contrast injections and drug delivery. For example, secondary branch 13 may also be used for flushing the system with saline, or any other appropriate uses. Secondary branch 13 of side arm body 10 is formed, in one embodiment, at approximately a 60 degree angle from primary branch 11. The invention is not limited by the angle at which secondary branch 13 connects with primary branch 11. A port 17 is formed at the end of secondary branch 13, and this port 17 provides connections for injections and other drug or fluid delivery devices.

Referring to FIGS. 1a to 1d, 2, and 4a, a finger rest 19 is formed on the exterior surface of secondary branch 13. Finger rest 19 is formed, in one embodiment, at approximately 30 degrees from secondary branch 13. In another embodiment, the angle at which finger rest 19 is formed may be 20 degrees, 40 degrees, or any other suitable angle. The invention is not limited by the angle at which finger rest 19 connects with secondary branch 13. Finger rest 19 is sufficiently large enough to fit at least one finger of an adult user of bleed back control assembly 1. Finger rest 19 provides the user with improved gripping of bleed back control assembly 1, particularly when the user is operating cap assembly 30 as discussed further below.

In another embodiment, a finger rest 19 is formed on the exterior surface of primary branch 11 of side arm body 10. In this embodiment, the finger rest 19 on primary branch 11 may be either in place of, or in addition to, a finger rest 19 on secondary branch 13 of side arm body 10.

Primary branch 11 of the side arm body 10 has two ends: a proximal end 12 and a distal end 16. A seal cavity 14 is formed within proximal end 12 of primary branch 11 of side arm body 10. Seal cavity 14 is concentric with, and provides access to, lumen 18 formed axially through primary branch 11.

Seal cavity 14 has a wider diameter than the diameter of lumen 18. In one embodiment, seal cavity 14's diameter is approximately 325% wider than the diameter of lumen 18. The invention is not limited by the difference between the diameters of seal cavity 14 and lumen 18.

In another embodiment, lumens 15 and 18 may taper or change diameters along their lengths. In one embodiment, the diameter of lumen 18 towards the proximal end of lumen 18 may be approximately 16% wider than the diameter at the distal end of lumen 18. The invention is not limited by whether lumens 15 or 18 taper, or by the amount by which each or either lumen tapers.

The exterior surface of seal cavity 14 has threads 21 to allow cap assembly 30 to rotatably connect to side arm body 10, as described further below.

Referring to FIGS. 1a, 2, 4a, and 4b, seal cavity 14 has an interior surface 23 which is adjacent to aperture 29 connecting seal cavity 14 to lumen 18.

Figure 2:
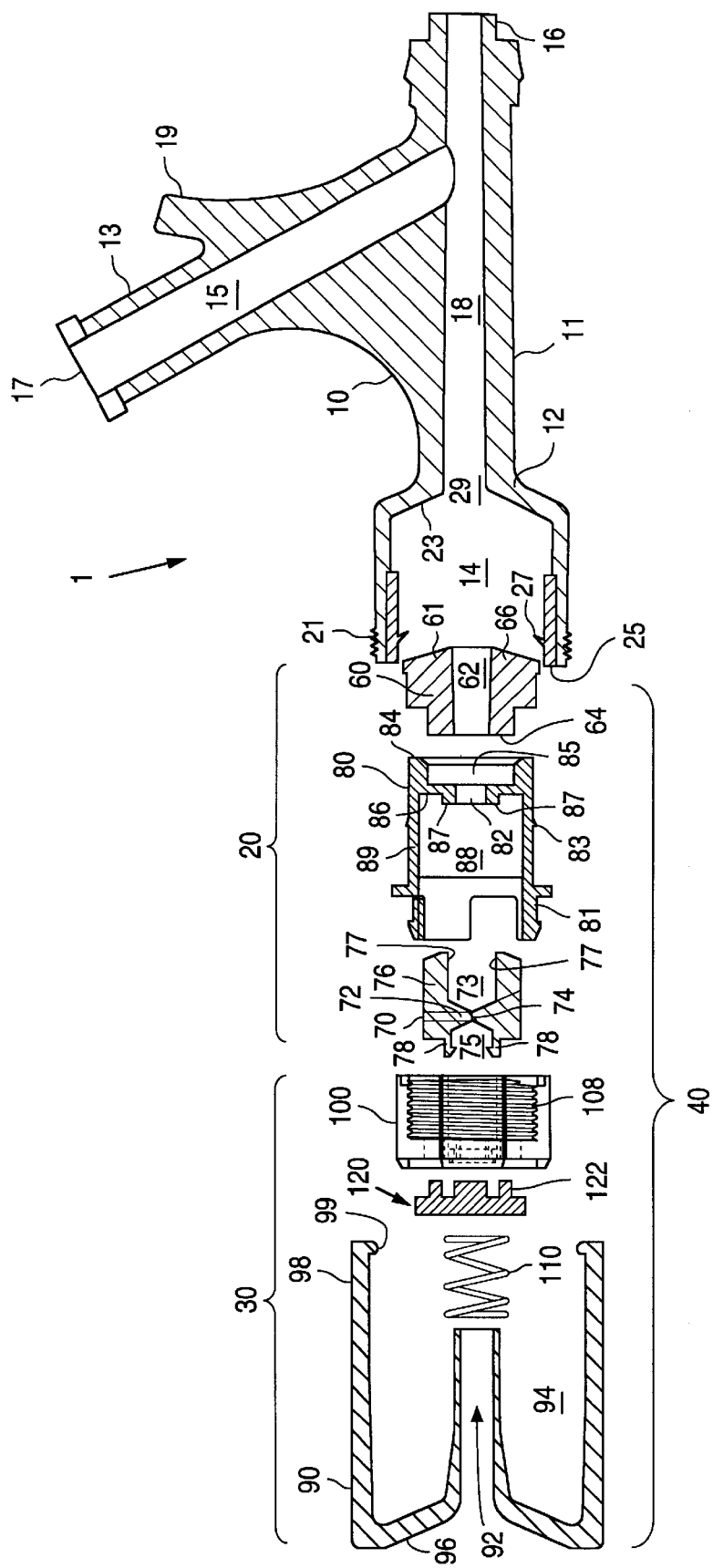
FIG. 2 is an exploded view of a seal body and side arm body of a bleed back control assembly in accordance with the present invention.
Figure 3:
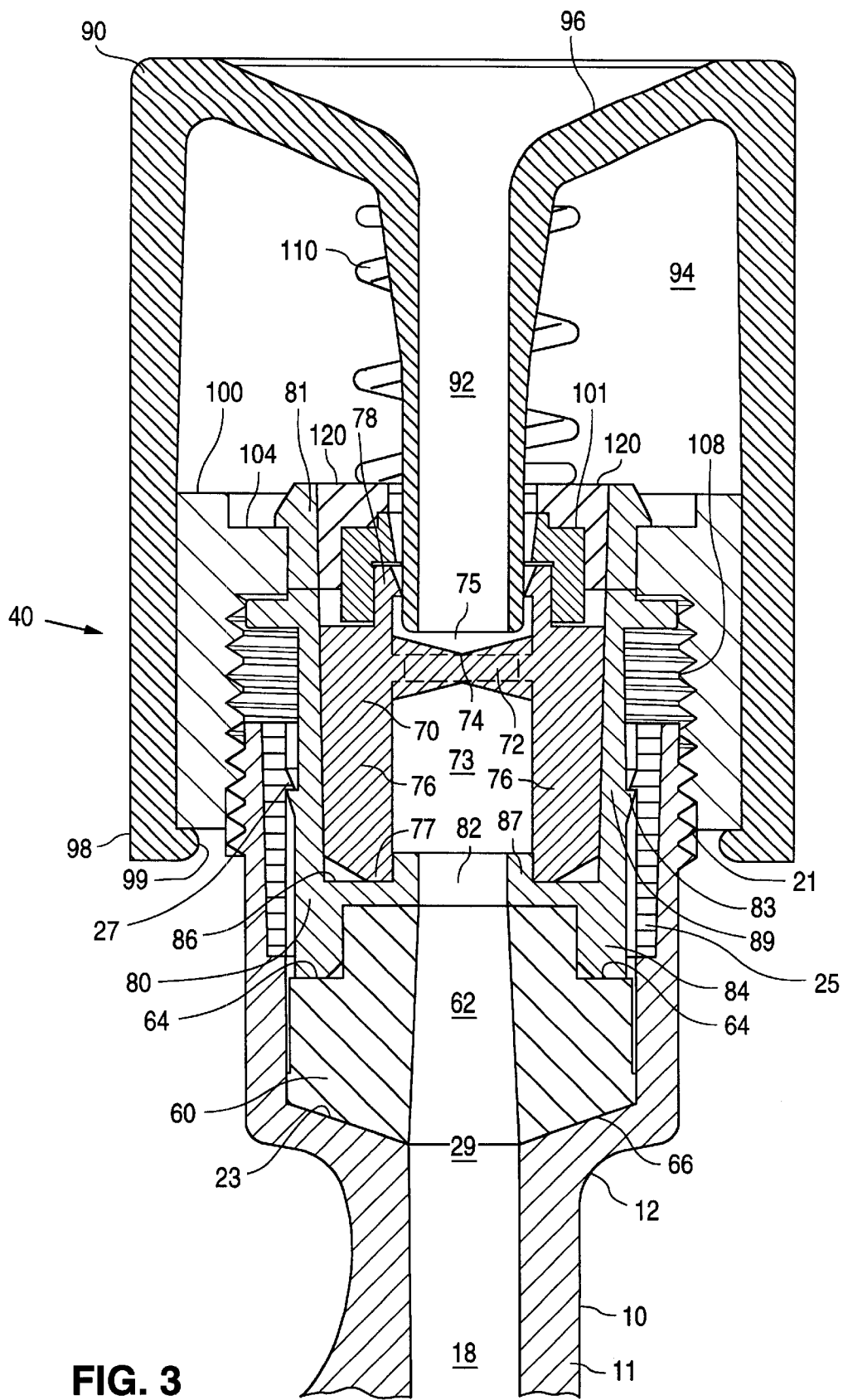
FIG. 3 is a cross-sectional view of a seal body and a proximal end of a side arm body of a bleed back control assembly in accordance with the present invention.
Figure 4A:
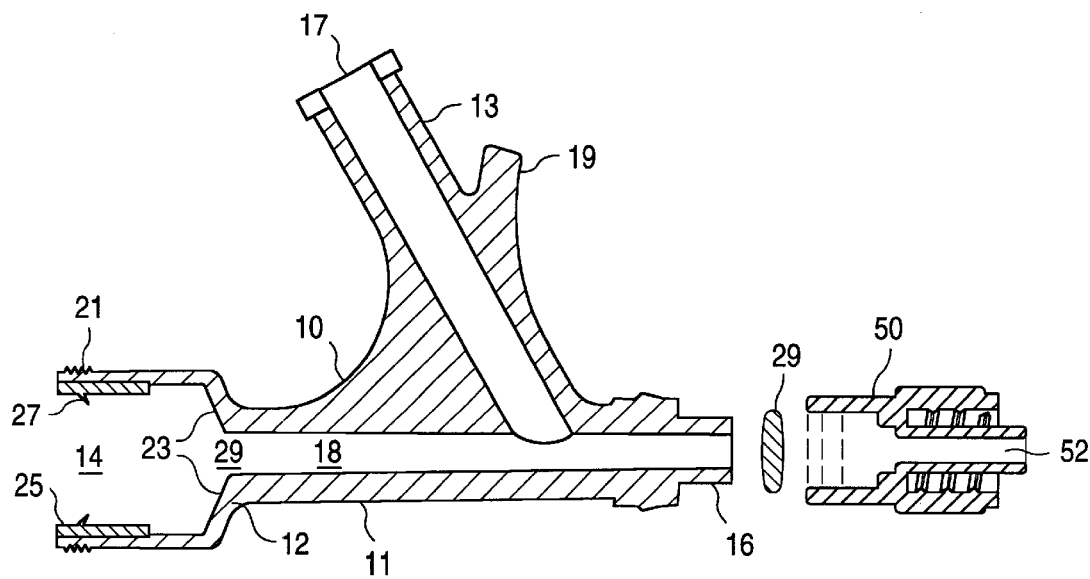
FIG. 4a is an exploded view and FIG. 4b is a cross-sectional view of a side arm body and male luer connector in accordance with the present invention.

In one embodiment as shown in FIGS. 2 and 4a, attached to interior surface 23 of seal cavity 14 is snap insert 25. As discussed further below in relation to FIGS. 3 and 11a to 11e, blocking notch 27 of snap insert 25 constrains the movement of seal assembly 20 within seal cavity 14 and inhibits the removal of seal assembly 20 from seal cavity 14. In an alternative embodiment, snap insert 25, including blocking notch 27, is integral with and formed as part of interior surface 23 of seal cavity 14.

Figure 4B:
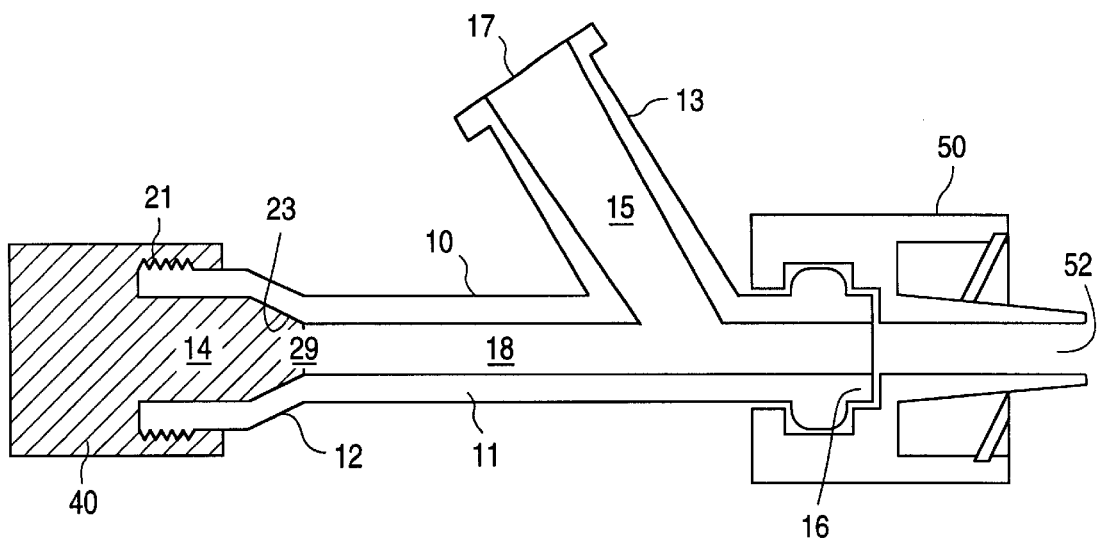

Referring to FIGS. 4a and 4b, distal end 16 of side arm body 10 is connected to a male luer connector 50. Luer connector 50 has a lumen 52 which connects proximally with the distal end of lumen 18. Male luer connector 50 may be 360 degrees rotatable or any other appropriate amount of rotation.

In one embodiment, an O-ring 29 is interposed at the connection between distal end 16 of side arm body 10 and luer connector 50. O-ring 29 improves the seal between side arm body 10 and luer connector 50.

O-ring 29 is a conventional O-ring gasket or seal formed of an appropriate elastic material. In one embodiment, O-ring 29 is formed of black color ethylene propylene diene monomer having a hardness of 70±5 Shore-A, with an interior diameter of approximately 0.176 inches. If O-ring 29 requires cleaning, a medical grade wash is used. O-ring 29 may be non-cytotoxic, and in an alternate embodiment may be non-allergenic.

An appropriate lubricant may be used with O-ring 29. Dow Corning 360 Medical Fluid, 350 centistoke viscosity (referred to as "Dow 360") may be used as a lubricant. In one embodiment, a mixture of alcohol and Dow 360 may be used as a lubricant for O-ring 29. Alternatively, O-ring 29 may be lubricated with a coating of a mixture of alcohol and dichloromethane followed by a successive coating of a mixture of alcohol, dichloromethane, and Dow 360.

While a luer connector 50 is shown connected to the distal end 16 of side arm body 10, the invention is not limited by whether any structures are connected to distal end 16 nor by what those structures are. Those of ordinary skill will appreciate that other appropriate devices may be connected to distal end 16 of side arm body 10 without departing from the scope of the invention. In an alternate embodiment, luer connector 50 is formed integrally as part of distal end 16 of side arm body 10.

Side arm body 10, snap insert 25, and luer connector 50 may be formed of any appropriate polymeric material (either thermoplastic or thermosetting). In one embodiment, side arm body 10, snap insert 25, and luer connector 50 are formed of polycarbonate, and may be formed of radiation grade or e-beamable polycarbonate.

The invention is not limited by the type of O-ring 29 or connector 50 used, nor by the type of lubricant used for O-ring 29.

Seal Body

Referring to FIGS. 1c and 1d, seal body 40 comprises seal assembly 20 connected to cap assembly 30, and cap assembly 30 is connected to the exterior surface of seal cavity 14. As discussed above, seal assembly 20 is held within seal cavity 14 and conforms to the shape of the interior surface 23 of seal cavity 14. Cap assembly 30 holds seal assembly 20 within seal cavity 14 and, as discussed below with respect to FIGS. 2, 4a, and 4b, cap assembly 30 is connected to the proximal end of side arm body 10. Thus, seal body 40 is a seal mechanism connected to proximal end 12 of side arm body 10 as further described below.

Referring to FIG. 2, seal assembly 20 comprises bleed back control seal 70, and seal holder 80. In another embodiment, seal assembly 20 comprises a clamp seal 60, along with bleed back control seal 70 and seal holder 80. Cap assembly 30 comprises funnel cap 90, threaded cap 100, return spring 110, and snap retainer 120. Thus, seal body 40 is a seal mechanism comprising one or more seals, such as bleed back control seal 70, as well as seal holder 80, and two caps, funnel cap 90 and threaded cap 100, as well as spring 110 and snap retainer 120.

FIG. 2 shows these components in exploded view, and FIG. 3 shows these components assembled in relation to each other, as well as in relation to the proximal end 12 of side arm body 10. In the orientation of FIG. 3, the proximal end of the seal body 40 is shown at the top of the figure. Each component will be discussed in turn.

a. Clamp Seal

Referring to FIGS. 2, 3, 7a and 7b, clamp seal 60 is shaped as three successively larger concentric cylinders, comprising cylindrical portions 63, 65, and 67, with a frustrum portion 61 connected distally to cylindrical portion 63. The cylindrical portion 63 thus tapers at the distal end to a frustrum portion 61. Clamp seal 60 fits within seal cavity 14 and conforms generally to the diameter and shape of the bottom of interior surface 23 of seal cavity 14. In one embodiment, there may be a gap or space between clamp seal 60 and the distal interior portion 23 of seal cavity 14, when clamp seal 60 has not been closed or operated on by the user. Clamp seal 60 has a lumen 62 formed through the cylindrical portions 63, 65, and 67, as well as frustrum portion 61. Lumen 62 is in fluid communication with lumen 18 of side arm body 10.

In one embodiment, the maximum diameter of distal cylindrical portion 63 (as well as the diameter of the bottom frustrum portion 61) of clamp seal 60 is larger than the interior diameter of the corresponding portion of seal cavity 14. In addition, the maximum diameter of proximal cylindrical portion 67 of clamp seal 60 is larger than the interior diameter of the corresponding portion of distal seal holder cavity 85 of seal holder 89. The invention is not limited by the precise differential between the diameters of clamp seal 60 and the interior diameter of seal cavity 14 or distal seal holder cavity 85. This difference in diameters results in the walls of seal cavity 14 providing compression and support to the distal cylindrical portion 63 of clamp seal 60, and ensures that distal cylindrical portion of clamp seal 60 provides a seal inhibiting fluids or gases from escaping around the distal outside surface of seal clamp 60. In addition, the difference in diameters between proximal cylindrical portion 67 of clamp seal 60 and distal seal holder cavity 85 results in the walls of distal seal holder cavity 85 providing compression and support to clamp seal 60, and ensures that cylindrical portion 67 inhibits fluids or gases from escaping around the proximal exterior surface of clamp seal 60.

As discussed below in relation to FIGS. 11a to 11e, a user may open and close clamp seal 60 by turning threaded cap 100. Thus, clamp seal 60 may be opened and closed selectively. In its open, disengaged position, clamp seal 60 creates a seal inhibiting the flow of fluids or gases into seal body 40 other than through lumen 62 of clamp seal 60. Clamp seal 60 also acts as a bridge or transition joint between seal body 40 and side arm body 10.

As discussed, clamp seal 60 has a lumen 62 formed axially therethrough which is concentric with lumen 18 of side arm body 10. Lumen 62 tapers such that the top (or proximal) aperture of lumen 62 has a smaller diameter than the bottom (or distal) aperture of lumen 62. In one embodiment, the top aperture of lumen 62 is approximately 85% as wide as the bottom aperture of lumen 62. The bottom aperture of lumen 62 has a slightly larger diameter than the diameter of aperture 29 connecting to lumen 18 of primary shaft 11 of side arm body 10. In one embodiment, the bottom aperture of lumen 62 of clamp seal 60 has a diameter larger than the diameter of aperture 29 leading to lumen 18 of side arm body 10. Also, the proximal aperture of lumen 62 of clamp seal 60 has a diameter larger than the diameter of aperture 82 of seal holder 80. These differences in diameters provide rebound so that clamp seal 60 does not get stuck in lumen 18 or in aperture 82 of seal holder 80.

The interior surface 23 of seal cavity 14 and the tapered frustrum 61 of clamp seal 60 are, in this embodiment, both at approximately a 20 degree angle from the plane of the distal (or bottom) aperture of lumen 62. Those of ordinary skill will appreciate that the invention is not limited by the angle of either interior surface 23 or clamp seal 60's frustrum portion 61, nor by the amount of taper in lumen 62.

Clamp seal 60 is formed of an elastic and resilient material, such as an appropriate elastomeric substance. In one embodiment, clamp seal 60 is made of black color fluorosilicone having a hardness of 35±5 Shore-A. Clamp seal 60 is, in this embodiment, post cured for 4 hours at 400 degrees Fahrenheit. Clamp seal 60 may be cleaned by any conventional method known to those of ordinary skill, if needed. Additionally, soap water may be used as a mold release prior to cleaning, if any. If cleaning is performed, a 50/50 mixture of alcohol and deionized water may be used. If clamp seal 60 is formed of a synthetic ductile material, clamp seal 60 may be non-allergenic, and in an alternate embodiment may be non-cytotoxic.

An appropriate lubricant may be used with clamp seal 60. Dow 360 by itself may, however, exhibit some adhering properties within lumen 62 of clamp seal 60 over time or at an elevated temperature. In one embodiment, a mixture of alcohol and Dow 360 may be used as a lubricant for clamp seal 60, and this mixture may bond to some extent to the surface of clamp seal 60. Alternatively, clamp seal 60 may be lubricated with a coating of a mixture of alcohol and dichloromethane, followed by a successive coating of a mixture of alcohol, dichloromethane, and Dow 360. The invention is not limited by the type (or presence) of lubricant used for clamp seal 60.

In one embodiment, clamp seal 60 forms part of seal assembly 20. In another alternate embodiment, seal assembly 20 does not include clamp seal 60. One of ordinary skill will understand that, in this embodiment, the absence of seal clamp 60 may result in minor alterations in seal holder 80 or cap assembly 30.

b. Seal Holder

Referring to FIGS. 2, 3, 6a, and 6b, within seal body 40 seal holder 80 is placed between clamp seal 60 and bleed back control seal 70. Seal holder 80 has an aperture 82 formed in its bottom surface, and this aperture 82 is concentric with lumen 62 of clamp seal 60. In one embodiment, aperture 82 of seal holder 80 has a diameter smaller than the diameter of the proximal (or top) aperture of lumen 62 of clamp seal 60.

Seal holder 80 terminates distally with bottom arms 84. Arms 84 conform substantially with the shape of the proximal surface 64 of clamp seal 60. As described below, arms 84 of seal holder 80 provide axial and radial compression to clamp seal 60.

As discussed above, seal holder 80 has a distal seal holder cavity 85 formed distal to aperture 82 and defined by the distal portion of arms 84. As discussed above, proximal cylindrical portion 67 of clamp seal 60 is set within distal seal holder cavity 85.

Figure 6B:
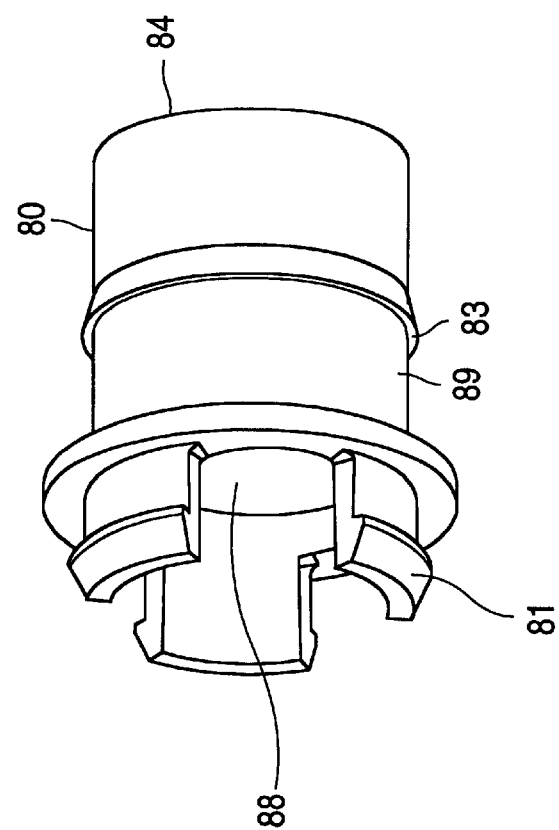
FIG. 6a is a cross-sectional view and FIG. 6b is a perspective view of a seal holder in accordance with the present invention.
Figure 6A:
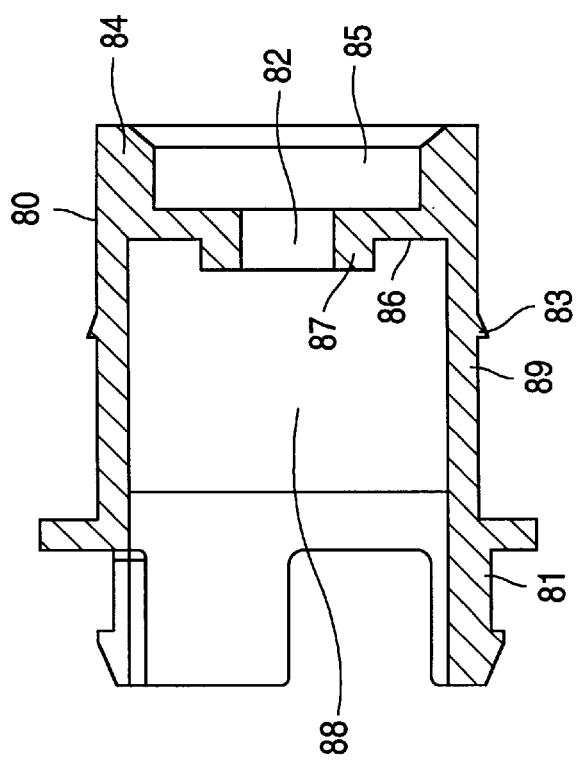
Figure 7A:
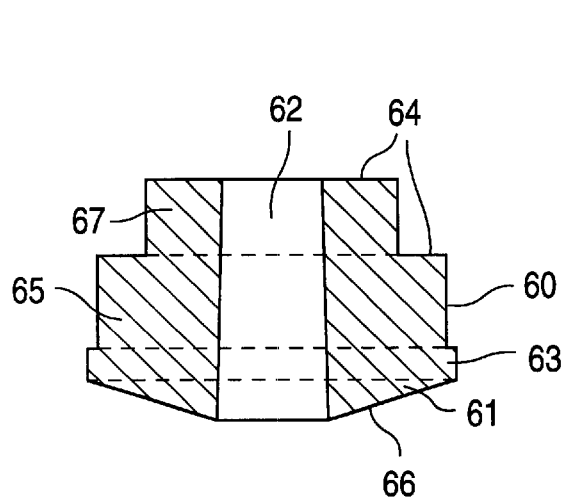
FIG. 7a is a cross-sectional view and FIG. 7b is a perspective view of a clamp seal in accordance with the present invention.
Figure 7B:
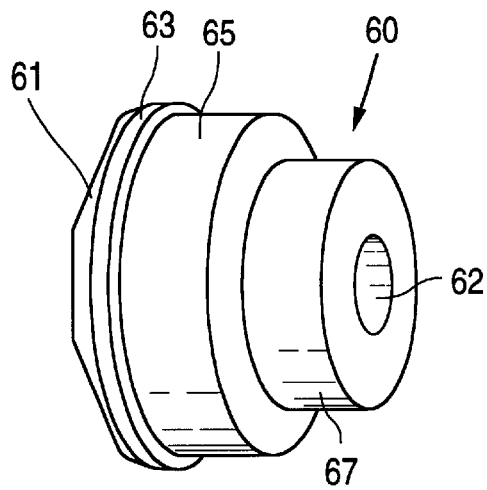

Referring to FIG. 6a, horizontal legs 86 extend laterally from arms 84. Legs 86 form the proximal wall of distal seal holder cavity 85. Referring to FIGS. 2 and 3, legs 86 of seal holder 80 are interposed between the proximal surface 64 of clamp seal 60 and the distal arms 76 of bleed back control seal 70.

Risers 87 are formed at the ends of legs 86 and protrude proximally. Legs 86 and risers 87 are formed so that aperture 82 is formed therethrough. The distal (or bottom) surface of legs 86 conform substantially with the shape of the proximal (or top) surface 64 of clamp seal 60. The proximal (or top) surface of legs 86 support and conform substantially to the distal (or bottom) surface of distal portion 77 of arms 76 of bleed back control seal 70. In one embodiment, distal portions 77 may bevel inward as shown for example in FIGS. 2 and 3. Risers 87 prevent compression of distal portions 77 of bleed back control seal 70 into aperture 82.

Seal holder 80 has a proximal interior chamber 88 which is defined by walls 89. Interior chamber 88 is in fluid communication with lumen 62 of clamp seal 60, by virtue of aperture 82. Bleed back control seal 70 is supported within interior chamber 88. The diameter of top or proximal interior chamber 88 is slightly smaller than the diameter of bleed back control seal 70. Accordingly, walls 89 of seal holder 80 provide axial and radial support, as well as compression (axial and radial), for bleed back control seal 70. In one embodiment, the diameter of top or proximal interior chamber 88 is approximately 6% smaller than the diameter of bleed back control seal 70. The invention is not limited by a precise ratio of the diameters of interior chamber 88 of seal holder 80 and bleed back control seal 70.

c. Bleed Back Control Seal

Referring to FIGS. 2, 3, 5*a*, 5*b*, and 5*c*, bleed back control seal 70 has distal (or bottom) side arms 76, a web area 72 formed between arms 76, distal portions 77 of arms 76, and upper ears 78. Bleed back control seal 70 is, in one embodiment, substantially in the shape of two concentric cylinders each having a lumen, with a bottom (or distal) chamber 73 divided from a top (or proximal) chamber 75 by web area 72. Web area 72 is formed at the proximal or top end of chamber 73 of the larger, bottom (or distal) cylinder formed by side arms 76. The diameter of the top cylinder formed by ears 78 is smaller than the diameter of the bottom cylinder formed by side arms 76. In one embodiment, chamber 73 formed between side arms 76 has a diameter larger than the diameter of chamber 75 formed between ears 78.

As discussed further below in relation to FIGS. 3 and 13*a* to 13*d*, funnel cap 90 comprises a dilator 92 which is a tube having a lumen extending from the proximal end of funnel cap 90 to top chamber 75 of bleed back control seal 70. Dilator 92's distal end is held within top chamber 75 of bleed back control seal 70, unless dilator 92 is moved. As discussed further below, the user can move dilator 92 distally, and thus cause bleed back control seal 70 to dilate or open. However, in the unactivated or normal state, dilator 92 rests close to, but does not impact, web area 72 of bleed back control seal 70.

Ears 78 of bleed back control seal 70 are shaped to conform with the diameter and shape of dilator 92. The ears 78 of bleed back control seal 70 have an interior diameter smaller than the exterior diameter of dilator 92. This difference in diameters ensures that ears 78 provide a seal and inhibit fluids or gases from escaping proximally around the exterior surface of dilator 92. The proximal end of ears 78 are formed to surround dilator 92 when dilator 92 is in both its disengaged and engaged positions. Ears 78 will surround and seal around the exterior of dilator 92 when threaded cap 100 is screwed down or tightened (as discussed below in relation to FIGS. 11*a* to 11*e*, screwing or tightening threaded cap 100 has the effect of moving both bleed back control seal 70 and seal holder 80 distally). Thus, ears 78 of bleed back control seal 70 form a seal around the exterior surface of dilator 92 regardless of how the user manipulates cap assembly 30.

In one embodiment, the proximal end of ears 78 may be notched at an angle of approximately 30 degrees to improve seal integrity and aid in alignment of dilator 92 of funnel cap 90. Thus, integrated into bleed back control seal 70 is a seal formed by ears 78 surrounding dilator 92 in order to prevent or inhibit fluid or gas leakage into interior chamber 94 of funnel cap 90.

Bleed back control seal 70 may thus inhibit the introduction of fluids or gases into interior chamber 94 of funnel cap 90. For some users of bleed back control assembly 1, in some circumstances, it may be undesirable to allow blood or other fluid to enter interior chamber 94 of funnel cap 90, because of a potential increased risk of confusion as to whether bleed back control assembly 1 is leaking. Fluid leakage into interior chamber 94 of funnel cap 90 may also make it more difficult to engage or depress funnel cap 90 so as to move dilator 92, as discussed below. Finally, if blood or other fluid were to collect in interior chamber 94 of funnel cap 90, trapped fluid may leak or spurt out of funnel cap 90 when the user depresses or engages funnel cap 90.

Figure 5A:
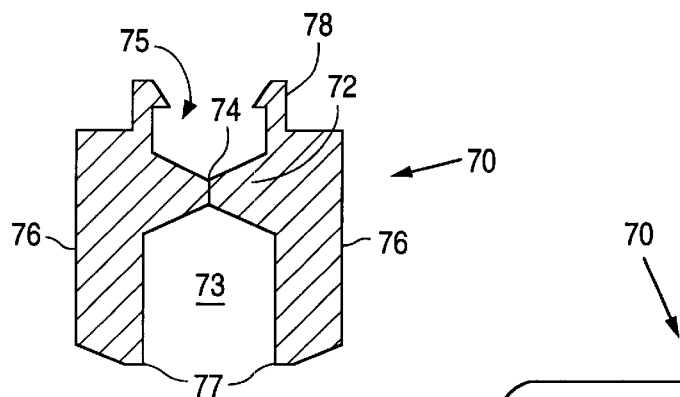
FIG. 5a is a cross-sectional view and FIG. 5b is a perspective view of bleed back control seal in accordance with the present invention.
Figure 5B:
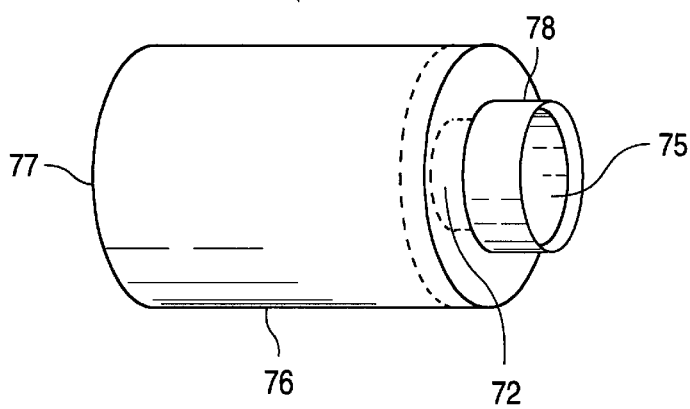

As noted above, bleed back control seal 70 has a web area 72 dividing top chamber 75 from bottom chamber 73. Web area 72 is roughly perpendicular to the plane of ears 78 and is located distal to ears 78. Web area 72 may be regarded as both the floor of top chamber 75 and the ceiling of bottom chamber 73 of bleed back control seal 70. As shown in FIG. 5*b*, web area 72 is substantially disc shaped.

Web area 72 is thinner at the center and thicker towards the side arms 76. In one embodiment as shown for example in FIGS. 2, 3, and 5*a*, the cross-section of web area 72 is approximately wedge shaped. A wedge shaped cross-section of web area 72 provides support for seal integrity. In one embodiment, the wedge may be formed at an angle of approximately 115 degrees from the plane of side arms 76. However, one of ordinary skill would appreciate that the angle of the wedge may differ, and the invention is not limited by the precise angle of the wedge.

The thinning of web area 72 towards the center provides a balance between sealing and ease of vascular intervention device movement through web area 72. This change in thickness of web area 72 also resists tearing of web area 72 as a vascular intervention device is inserted through web area 72. In one embodiment, web area 72 thins at the middle to a width of approximately 0.023 to 0.031 inches. The invention is not limited by the exact width of web area 72 or the angle of the wedge cross-section of web area 72.

In the center of web 72 is aperture 74. In one embodiment, aperture 74 is formed as a pinhole completely intersecting web area 72. Aperture 74 is concentric with lumen 18 of the primary shaft 11 of side arm body 10, as well as lumen 62 of clamp seal 60. As noted above, the user may push funnel cap 90 and dilator 92 distally. By moving dilator 92 distally, a user will cause dilator 92 to stretch the elastomeric material of web area 72, thus causing aperture 74 to dilate or open wider.

In the normal, disengaged position, in which dilator 92 does not impact web area 72, aperture 74 of bleed back control seal 70 is closed and inhibits the passage of fluid through bleed back control seal 70. In the closed position, bleed back control seal 70's web area 72 inhibits fluid communication between bottom chamber 73 and top chamber 75. Ultimately, in the closed or normal position, web area 72 of bleed back control seal 70 inhibits bleed back or loss of fluid from primary lumen 18 to dilator 92 of funnel cap 90.

In the closed position, bleed back control seal 70 can withstand fluid pressures of roughly 40–100 psi. The invention is not limited by the precise fluid pressures which bleed back control seal 70 may withstand. The resistance of bleed back control seal 70 to fluidic pressure may be increased depending on the elastic material used for forming bleed back control seal 70 or on the dimensions of seal 70, including thickness of web area 72 and precise configuration of aperture 74.

Figure 5C:
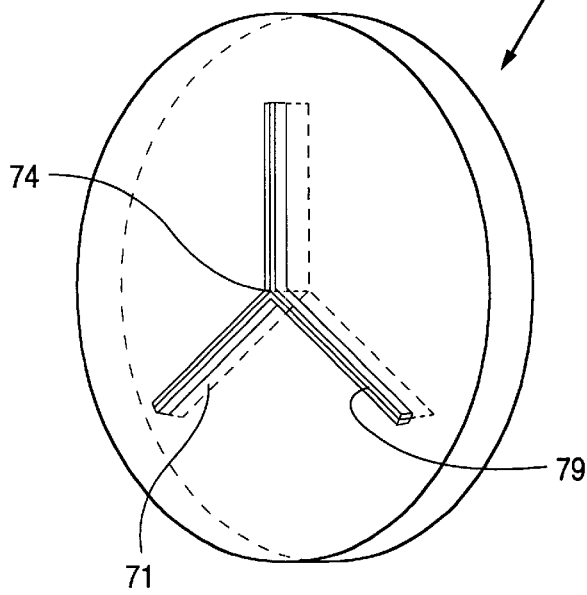
FIG. 5c is a perspective view of a web area of a bleed back control seal in accordance with another embodiment of the present invention.

In an alternate embodiment, web area 72 may have an aperture 74 which may be formed with slits 71 and flaps 79 in a star or tricuspid shape as shown in FIG. 5c. By using this star shaped embodiment of aperture 74, bleed back control seal 70 may increase resistance to fluid pressures up to approximately 500 psi.

Figure 5D:
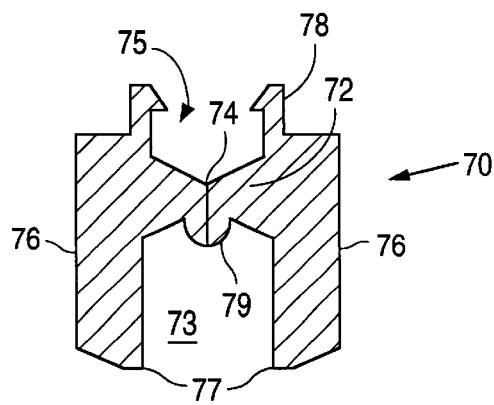
FIG. 5d is a cross-sectional view of a bleed back control seal in accordance with another embodiment of the present invention.

In an alternate embodiment, web area 72 may include a spherical portion 79 connected in the center of the distal surface of web area 72, as shown in FIG. 5d. In this embodiment, aperture 74 extends through spherical portion 79. By using this spherical portion 79 as a pressure dome, bleed back control seal 70 may then ease resistance to fluid pressures to approximately 400 psi.

Bleed back control seal 70 extends distally with arms 76. Arms 76 have distal portions 77. In one embodiment, distal portions 77 may bevel inward, and the invention is not limited by the amount or presence of bevel of distal portions 77. As discussed above, the proximal surface of legs 86 of seal holder 80 support the bottom or distal portions 77 of bleed back control seal 70. Legs 86 terminate in risers 87. The proximal surface of legs 86 are shaped to conform substantially to and engage with the distal surface of distal portions 77 of arms 76 of bleed back control seal 70. Risers 87 prevent compression of distal portions 77 of bleed back control seal 70 into aperture 82 of seal holder 80. Legs 86 and risers 87 of seal holder 80 also provide rigidity, support, and compression to bleed back control seal 70. Bleed back control seal 70 is held within chamber 88 formed by legs 86, risers 87, and walls 89 of seal holder 80.

Bleed back control seal 70 is made from a suitably elastic polymeric material. In one embodiment, bleed back control seal 70 is made of natural yellowish color polyisoprene having a hardness of 30±5 Shore-A and elongation of approximately 750%. In another embodiment, bleed back control seal 70 may be formed of a synthetic latex, silicone, or rubber. Bleed back control seal 70 may be sterilized by conventional techniques such as e-beam or ethylene oxide sterilization. Bleed back control seal 70 may be cleaned, if wanted, by any conventional cleaning method known to those of ordinary skill. Bleed back control seal 70 is formed of a synthetic resilient material, and bleed back control seal 70 may be non-cytotoxic, and in an alternate embodiment may be non-allergenic.

Those of ordinary skill will understand that other elastic or resilient materials may be suitable for bleed back control seal 70. In one embodiment, polyisoprene, manufactured by Lexington Medical, of 30 durometer medical grade may be used.

The elasticity of the material of bleed back control seal 70 causes web area 72 to form and seal around a vascular intervention device introduced through dilator 92, then into top chamber 75, then through aperture 74, and then through bottom chamber 73 of bleed back control seal 70. Thus, bleed back control seal 70 is self-sizing and prevents fluid loss or bleed back, while still allowing movement of a vascular intervention device through bleed back control assembly 1. A user may introduce any appropriate vascular intervention device 130 into bleed back control assembly 1, such as a catheter (for example, a balloon catheter, an atherectomy catheter, a guidewire, or a stent with delivery system). The elasticity of web area 72 and bleed back control seal 70 generally allows a seal to form around any inserted devices 130. Bleed back control seal 70 is formed of an elastomer with elongation, resilience, and elasticity properties which are sufficient to allow dilation and constriction of bleed back seal 70, as well as insertion of devices 130 through aperture 74 of web area 70, without losing seal integrity. For example, polyisoprene allows approximately 750% elongation.

Those of ordinary skill will appreciate that bleed back control seal 70 can be of varying dimensions. For example, the diameter of bottom chamber 73 formed by side arms 76 and the angle of the wedge cross-section of web area 72 may be changed to improve efficiency. Thus, for example, increasing the diameter of bottom chamber 73 formed by side arms 76 may facilitate movement of dilator 92 of funnel cap 90 or devices 130 through the aperture 74 of bleed back control seal 70.

One of ordinary skill will appreciate that any suitable lubricant may be used for bleed back control seal 70. Surface tack may be removed by gas chlorinating at 800±100 parts per million. However, chlorinating may affect device movement or sealing through seal 70. Alternatively, a polydimethyl siloxane liquid lubricant may be used. In one embodiment, Dow 360, 350 centistoke viscosity, may be used as a lubricant. Alternatively, a coating of paralene may be used as a lubricant, or a suitable lubricant may be bonded into the surface of the material of bleed back control seal 70. The invention is not limited by the type (or presence) of lubricant used with bleed back control seal 70.

Referring to FIGS. 1d, 2, and 9a through 9c, within seal body 40, as noted above, bleed back control seal 70 is held within interior chamber 88 of seal holder 80 and is held distal to threaded cap 100. Interior arms 101 of threaded cap 100 engage the proximal (or top) end of bleed back control seal 70, such as the exterior surface of ears 78. Interior arms 101 of threaded cap 100 thus retain bleed back control seal 70 and keep bleed back control seal 70 placed within interior chamber 88 of seal holder 80.

In an alternate embodiment, interior arms 101 may be formed of an appropriate size and shape so as to provide rigidity and compression (either axial, radial, or both) to bleed back control seal 70, including ears 78.

Figure 8:
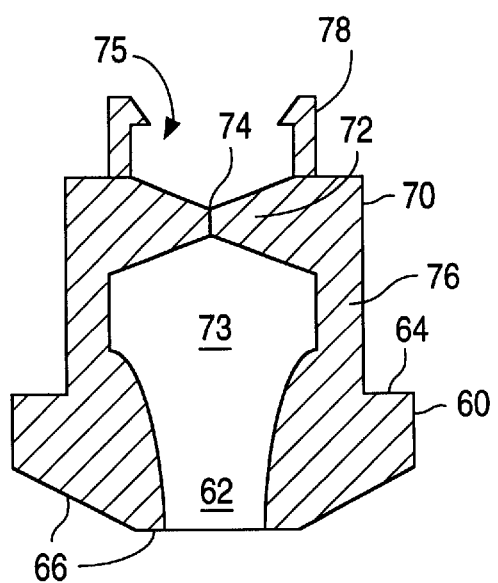
FIG. 8 is a cross-sectional view of a combined bleed back control seal and clamp seal in accordance with another embodiment of the present invention.
Figure 10A:
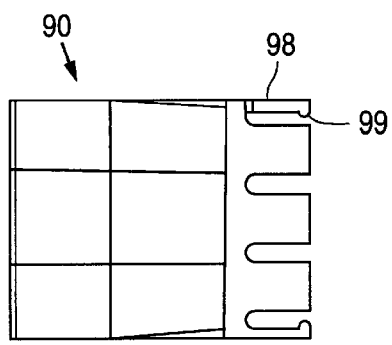
FIG. 10a is a side view.
Figure 10B:
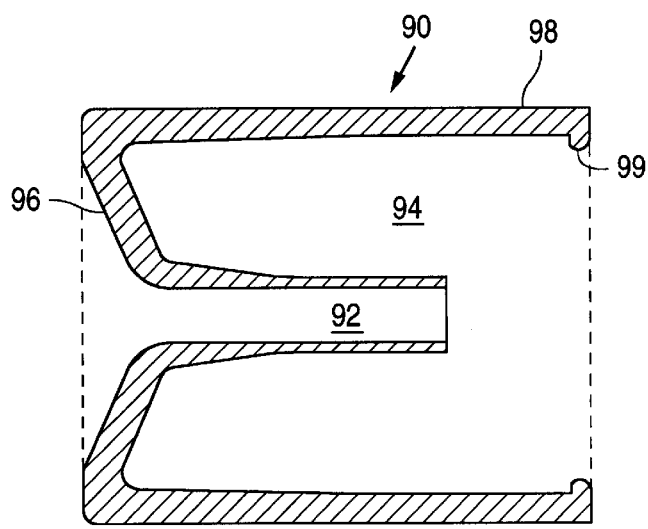
FIG. 10b is a cross-sectional view.
Figure 10C:
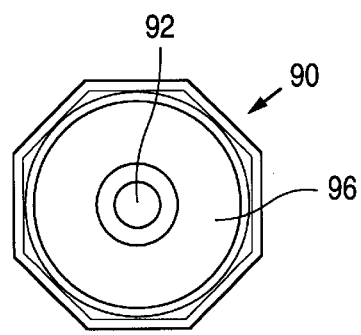
FIG. 10c is a top view of a funnel cap in accordance with the present invention.

Referring to FIG. 8, in an alternate embodiment, both clamp seal 60 and bleed back control seal 70 may be formed of one combined, integral seal structure. This combined clamp seal 60 and bleed back control seal 70 performs all the functions of these two seals all in one structure. In this embodiment, the combined clamp seal 60 and bleed back control seal 70 may be formed of any suitable material, for example, 30 or 45 durometer polyisoprene, fluorosilicone, silicone, or a blend of any of a plurality of appropriate resilient or elastic materials. In this embodiment, threaded cap 100 and seal holder 80 may, but need not, be combined in one integrated structure as well.

Thus, seal assembly 20 of seal body 40 comprises, in one embodiment, clamp seal 60, bleed back control seal 70, and seal holder 80. Cap assembly 30 of seal body 40 will be discussed next.

d. Funnel Cap, Dilator, and Return Spring

Cap assembly 30 comprises two concentric caps, funnel cap 90 and threaded cap 100, as well as spring 110 and snap retainer 120. Funnel cap 90 is proximal to and envelops threaded cap 100. Funnel cap 90 and threaded cap 100 may be any suitable approximately cylindrical shapes, and in one embodiment may be octagonal cylinders.

Referring to FIGS. 2, 3, and 10a to 10c, funnel cap 90 includes dilator 92 formed in the interior chamber 94 of funnel cap 90. Dilator 92 has a lumen extending distally away from funnel surface 96 of funnel cap 90. Dilator 92 is concentric with lumen 18 of side arm body 10. Dilator 92 is thus a tube with a lumen connecting (at the proximal end) the exterior of bleed back control assembly 1 with the interior of top chamber 75 of bleed back control seal 70 (at the distal end). Funnel cap 90 is proximal to bleed back control seal 70 and, in the disengaged position, the distal end of dilator 92 is proximal to and slightly separated from web area 72 of bleed back control seal 70. Dilator 92's lumen, in one embodiment, does not taper or change diameter, but those of ordinary skill will appreciate that dilator 92's lumen may taper or widen without departing from the scope of the invention.

Funnel cap 90 has a proximal exterior surface which tapers in the center to form the shape of a funnel 96 leading into the lumen of dilator 92. Funnel 96 of funnel cap 90 is concentric with the lumen of dilator 92. The maximum diameter of funnel 96, in one embodiment, may be approximately 73% of the diameter of the proximal surface of funnel cap 90. The invention is not limited by the precise ratio of the diameters of the funnel 96 and proximal surface of funnel cap 90. Funnel 96 improves the loading or self-locating of guidewires, catheters, and other devices 130 as the operator seeks to introduce them into bleed back control assembly 1. In one embodiment, funnel 96 may be formed at approximately a 25 degree angle from the plane of proximal surface of funnel cap 90. The invention is not limited by the angle at which funnel 96 is formed, nor by the diameter of funnel 96 as compared to the diameter of funnel cap 90.

Surrounding dilator 92 and disposed within interior chamber 94 of funnel cap 90 is return spring 110. The ends of spring 110 are squared. In one embodiment, spring 110 may have a spring rate of approximately 3.9 lbs./inch.

The proximal end of spring 110 abuts the interior surface of the proximal end of funnel cap 90. In one embodiment, the distal end of spring 110 abuts proximal surface 104 of threaded cap 100. In another embodiment, as discussed below, the distal end of spring 110 abuts and sits within proximal bowl 124 of snap retainer 120. In this embodiment, the placement of the distal end of spring 110 in bowl 124 helps stabilize and align spring 110, while spring 110 helps keep snap retainer 120 in place. In an alternate embodiment, the proximal surface of seal holder 80 may be formed to abut and support the distal end of spring 110.

The windings or coils of spring 110 surround the exterior surface of dilator 92. In one embodiment, spring 110 may have approximately five windings or coils. The invention is not limited by the diameter or spacing or number of the windings of spring 110. Spring 110 acts to return funnel cap 90 to the original or normal position when released, so that dilator 92 will not dilate aperture 74 of bleed back control seal 70 when the user releases funnel cap 90.

Spring 110 may be of any suitable material, and in one embodiment may be formed of 302 stainless steel wire. In one embodiment, the wire of spring 110 is approximately 0.018 inches in diameter, each winding of spring 110 is approximately 0.24 inches in diameter, and spring 110 is approximately 0.5 inches long in its uncompressed state. Spring 110 has ends which may be squared. The invention is not limited by the material out of which spring 110 is formed.

Funnel cap 90's exterior surface extends distally and terminates in arms 98. In an embodiment in which funnel cap 90 is octagonal, funnel cap 90 has eight arms 98. Overhanging lip 99 is formed at the distal edge or bottom of arms 98, and overhang 99 extends generally inward towards the interior chamber 94 of funnel cap 90. Overhang 99 of funnel cap 90 grips the distal surface of threaded cap 100 and thereby attaches funnel cap 90 to the exterior of threaded cap 100. Overhang 99 prevents funnel cap 90 from disengaging from threaded cap 100 by wrapping around the distal or bottom edge of threaded cap 100. Additionally, the arrangement of overhang 99 with threaded cap 100 allows funnel cap 90 to be moved distally, thus allowing dilator 92 to move distally as well through threaded cap 100 and bleed back control seal 70. Additionally, the arrangement of overhang 99 with threaded cap 100 allows funnel cap 90 to retain spring 110 in position, which in turn allows snap retainer 120 to be aligned and held in position. Additionally, the arrangement of funnel cap 90 with threaded cap 100 allows spring 110 to be held in a compressible manner, so as to allow spring 110 to return funnel cap 90 to its original or normal position after being released. The invention is not limited by the number of arms 98 or the shape of overhang 99, nor is the invention limited by the manner by which funnel cap 90 is connected to threaded cap 100.

e. Threaded Cap and Snap Retainer

Referring to FIGS. 2, 3, and 9a to 9c, in seal body 40 threaded cap 100 is interposed between funnel cap 90 and seal holder 80. Threaded cap 100 has a diameter such that threaded cap 100 fits the shape of the interior chamber 94 of funnel cap 90, and thus threaded cap 100 will conform inside funnel cap 90. The exterior surface of threaded cap 100 is, in one embodiment, octagonal, and similarly, in this embodiment, the interior surface of funnel cap 90 is octagonal as well. This arrangement allows a user to screw or twist threaded cap 100 by screwing or twisting the funnel cap 90, which thus results in axial movement of seal holder 80 and resulting compression or relaxation of clamp seal 60. Similarly, the arrangement of threaded cap 100 and funnel cap 90 allows funnel cap 90 to be moved by a user distally and proximally in an axial direction over the exterior surface of threaded cap 100, which thus results in axial movement of dilator 92 and resulting dilation or constriction of bleed back control seal 70.

Threaded cap 100 has a center hole 102 formed in its proximal surface 104. Threaded cap 100's center hole 102 has a diameter slightly wider than the diameter of dilator 92, and threaded cap 100's center hole 102 is concentric with the lumen of dilator 92. The distal end of dilator 92 of funnel cap 90 extends axially through center hole 102 of threaded cap 100.

Threaded cap 100 also has interior arms 101 which surround the center hole of threaded cap 100. Referring to FIG. 3, interior arms 101 are formed to conform to the shape of ears 78 and the proximal end of bleed back control seal 70.

Threaded cap 100 has secondary slots or apertures 106 formed in proximal surface 104 to allow seal holder 80 to attach to threaded cap 100. In one embodiment, there are three secondary apertures 106 which are shaped as curved slots and are spaced approximately equidistantly from each other around the same circumference. The proximal end of seal holder 80 ends in arms 81 which extend through secondary apertures 106 of threaded cap 100. Arms 81 have jaws which grip and envelop the portions of proximal surface 104 adjacent to secondary apertures 106. Arms 81 of seal holder 80 thus engage and connect to proximal surface 104 of threaded cap 100.

Figure 9A:
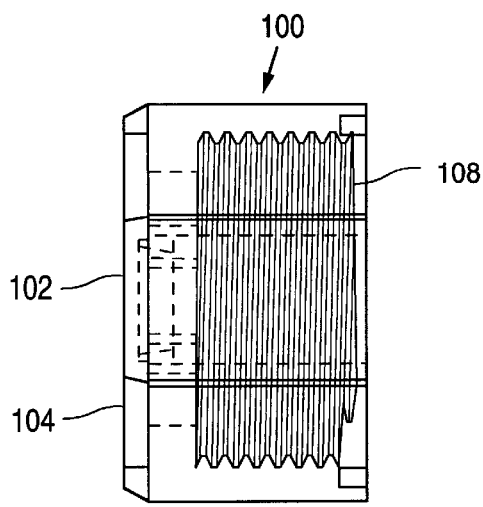
FIG. 9a is a side view.
Figure 9B:
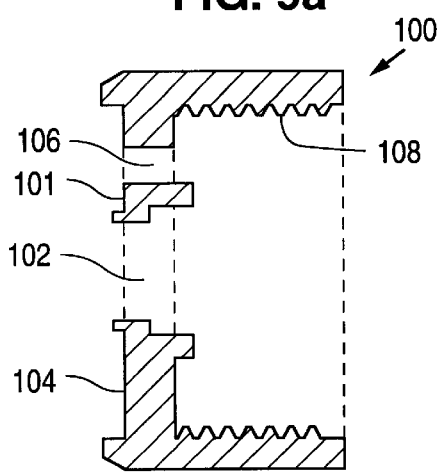
FIG. 9b is a cross-sectional view.
Figure 9C:
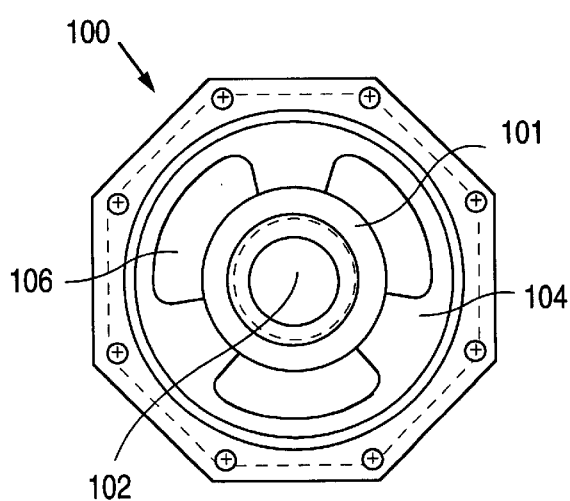
FIG. 9c is a top view of a threaded cap in accordance with the present invention.
Figure 9D:
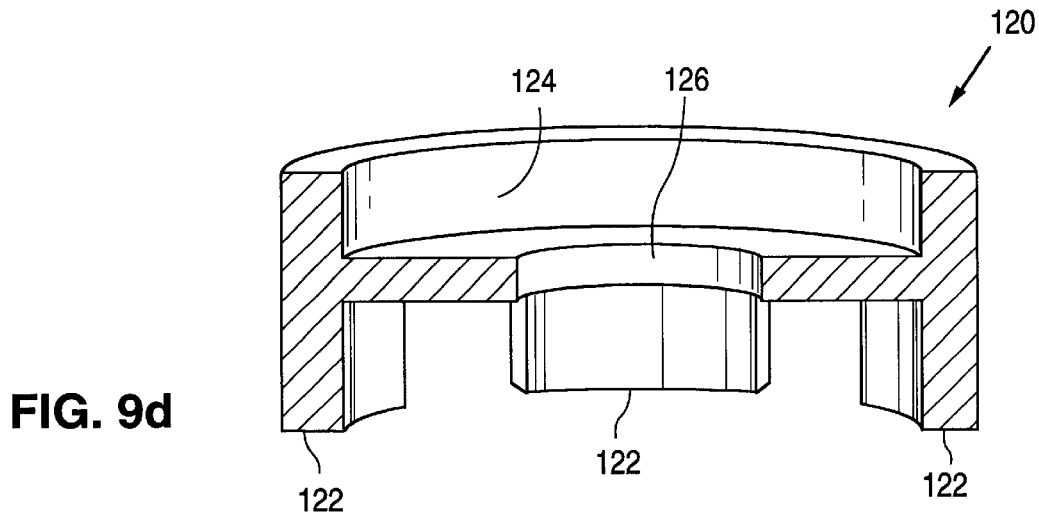
FIG. 9d is a cross-sectional view and FIG. 9e is a perspective view of a snap retainer in accordance with the present invention.
Figure 9E:
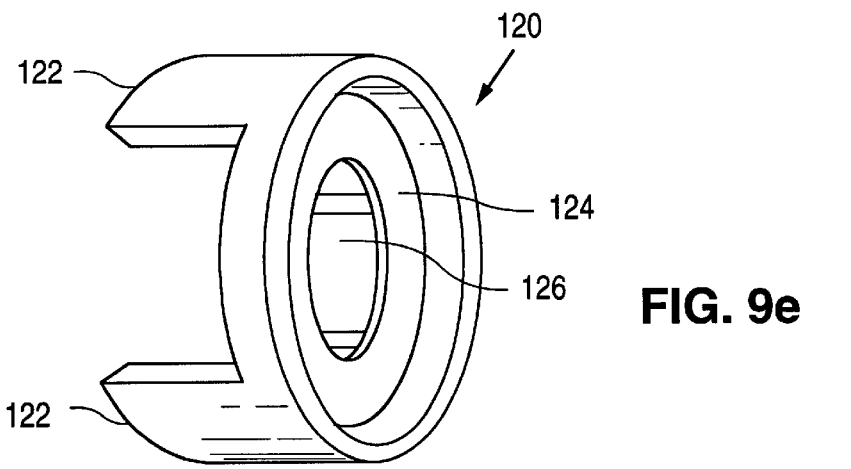
Figure 9F:
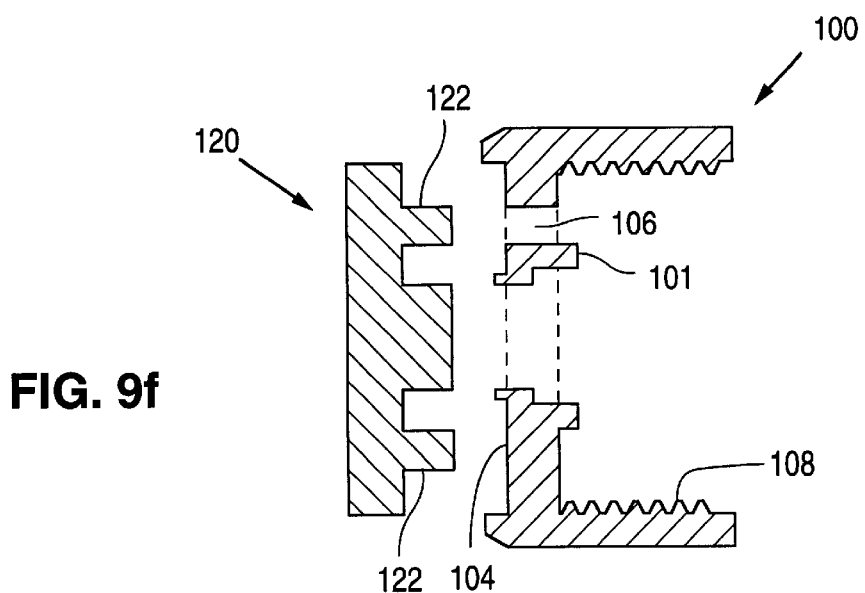
FIG. 9f is a cross-sectional view of a snap retainer and threaded cap in accordance with the present invention.

In one embodiment, a snap retainer 120 may be connected to threaded cap 100. In this embodiment, snap retainer 120 is connected to, and proximal to, threaded cap 100. Snap retainer 120 has a center hole 126 formed in its surface. Hole 126 of snap retainer 120 is concentric with center hole 102 of threaded cap 104. The diameter of snap retainer 120's center hole 126 is approximately equal to or greater than the diameter of center hole 102 of threaded cap 100. Center hole 126 of snap retainer 120 has a diameter greater than the maximum, exterior diameter of dilator 92 of funnel cap 90. Dilator 92 thus extends distally through center hole 126 of snap retainer 120 and then through center hole 102 of threaded cap 100. Referring to FIG. 9f, snap retainer 120 is concentric with threaded cap 100, and has an exterior maximum diameter slightly smaller than the diameter of the proximal portion of chamber 88 formed by arms 81 of seal holder 80. Snap retainer feet 122 of snap retainer 120 have an interior diameter slightly greater than the interior diameter of slots 106 of threaded cap 100, and thus feet 122 may fit in slots 106 behind arms 81 of seal holder 80. Snap retainer 120 also has an interior diameter larger than the exterior diameter of dilator 92 of funnel cap 90.

Snap retainer 120 has feet 122 which protrude distally. Feet 122 are formed to fit within each of apertures 106 of threaded cap 100. In one embodiment, there are three feet 122 which are curved and are spaced approximately equidistantly from each other around the same circumference. In another embodiment, feet 122 may be spaced from each other approximately 112 degrees, 112 degrees, and 136 degrees apart, if measured from midpoint to midpoint along their common circumference. Feet 122 are formed to fit within apertures 106 along with arms 81 of seal holder 80. Feet 122 sit interior to arms 81, and thus provide support to arms 81 and ensure that arms 81 retain a firm connection with surface 104 of threaded cap 100.

Snap retainer 120 also includes a proximal bowl 124. The distal end of return spring 110 sits within bowl 124 of retainer 120 without blocking the movement of dilator 92 through center hole 126. In this embodiment, proximal bowl 124 stabilizes and aligns spring 110. In turn, spring 110 holds snap retainer 120 in position atop threaded cap 100.

Threaded cap 100 has threads 108 formed in the interior surface of threaded cap 100. Threads 108 rotatably connect threaded cap 100 to side arm body 10, by connecting with threads 21 formed on the exterior surface of seal cavity 14.

As noted above, an alternate embodiment may comprise a seal assembly 20 which does not include clamp seal 60. In this alternate embodiment, seal holder 80 may be incorporated into proximal end 12 of side arm body 10. In this embodiment, snap retainer 120 and slots 106 of threaded cap 100 may no longer be necessary. In this embodiment, threaded cap 100 need not be rotatably attached to side arm body 10.

f. Miscellaneous

As shown in FIGS. 2, 3, and 9f, funnel 96 of funnel cap 90, dilator 92, center hole 126 of snap retainer 120, center hole 102 of threaded cap 100, aperture 74 in web area 72 of bleed back control seal 70, upper chamber 75 and lower chamber 73 of bleed back control seal 70, upper chamber 88 and distal cavity 85 and aperture 82 of seal holder 80, lumen 62 of clamp seal 60, and aperture 29 and lumen 18 of side arm body 10 are all substantially aligned along the same axis and are thus all essentially concentric.

Seal holder 80, funnel cap 90, threaded cap 100, and snap retainer 120 are all made of any suitable polymeric material, similar to side arm body 10, snap insert 25, and luer connector 50. In one embodiment, seal holder 80, funnel cap 90, threaded cap 100, and snap retainer 120 may be made of radiation grade polycarbonate.

Thus, the cap assembly 30 of seal body 40 comprises funnel cap 90, threaded cap 100, spring 110, and snap retainer 120. As discussed above, the user may operate cap assembly 30 to open or close seal assembly 20. The operation and interaction between cap assembly 30 and seal assembly 20 will be discussed next.

Operation of Clamp Seal

As noted above, one embodiment comprises a seal assembly 20 which does not include clamp seal 60. In an alternate embodiment, such as shown in FIGS. 2 and 3, clamp seal 60 may be included. In this alternate embodiment, operation of clamp seal 60 may be controlled by the user.

In this embodiment, clamp seal 60 may be opened or closed by the user. In the open position, clamp seal 60 allows fluids (such as blood) to pass through lumen 62 and will not impede the movement of devices (such as a catheter) through lumen 62. In the closed position, clamp seal 60 will substantially inhibit the flow of fluid (such as blood) through lumen 62, thus sealing aperture 29 connecting seal body 40 and side arm body 10. If a device (such as a catheter) has already been inserted through lumen 62, closing clamp seal 60 will cause lumen 62 to clamp around that device and hold that device in place. Operation of clamp seal 60 to open or close is discussed with reference to FIGS. 3, 11a to 11e, and 12a to 12d.

As noted above, turning threaded cap 100 causes clamp seal 60 to open and close. Proximal to and abutting the proximal surface 64 of clamp seal 60 is seal holder 80. Seal holder 80 has upper arms 81 which connect seal holder 80 to proximal surface 104 of threaded cap 100. Threaded cap 100 is rotatably connected to the exterior surface of seal cavity 14.

Threaded cap 100 may be rotated by the user to move threaded cap 100 axially towards or away from the distal end 16 of side arm body 10. Rotating or adjusting threaded cap 100 causes seal holder 80 to move axially as well. Rotation of threaded cap 100 to move distally is referred to as tightening, closing, or screwing of threaded cap 100; rotation of threaded cap 100 to move in the opposite, proximal direction is referred to as loosening, opening, or unscrewing threaded cap 100.

Rotating threaded cap 100 causes a corresponding axial movement of seal holder 80. When threaded cap 100 is tightened, the corresponding movement of seal holder 80 will cause the distal end 84 of seal holder 80 to compress seal clamp 60. Axial movement of seal holder 80 causes a corresponding compression (or closure) of clamp seal 60. A user's tightening of threaded cap 100 causes seal holder 80 to compress and deform clamp seal 80, which is made of an elastic material.

When threaded cap 100 is tightened, clamp seal 60 may be closed completely, when there is no device introduced within lumen 62 of clamp seal 60. As shown in FIGS. 11a to 11e, as threaded cap 100 is tightened, the material forming the walls of lumen 62 will deform and collapse or constrict lumen 62. Sufficient tightening of threaded cap 100 will cause the deformed frustum portion 61 of clamp seal 60 to enter and seal aperture 29 at the proximal end of lumen 18 of the primary shaft 11 of side arm body 10. Sufficient tightening of threaded cap 100 will also cause lumen 62 to constrict completely. Additionally, tightening of threaded cap 100 causes the cylindrical portions 63, 65, and 67 of clamp seal 60 to compress and deform, thus creating a seal around the exterior surface of clamp seal 60 where it impacts the interior walls of seal cavity 14. Thus, tightening threaded cap 100 will cause clamp seal 60 to close and inhibit the flow of fluid from side arm body 10 to the seal body 40.

Clamp seal 60 can be opened by unscrewing threaded cap 100. As threaded cap 100 and seal holder 80 are moved proximally, the resilient properties of the elastic material of clamp seal 60 will cause clamp seal 60 to return to its original shape and position.

Adjustment of threaded cap 100 to cause clamp seal 60 to close has several advantages. For example, it is undesirable for injections introduced through secondary branch 13 to exit side arm body 10 through proximal end 12, because the injected fluid will not be delivered to the patient. Closing clamp seal 60 allows the user to perform high pressure injections through secondary branch 13 of side arm body 10 while ensuring that the injected fluid does not exit side arm body 10 through proximal end 12. Typically, a user can generate up to approximately 200 psi for manual injections. In the closed position, clamp seal 60 can withstand up to at least approximately 400 psi, thus allowing the user to perform injections through lumen 15 of secondary branch 13 without allowing the fluid from these injections to exit side arm body 10 into seal body 40. In this way, injections through secondary branch 13 will be delivered into lumen 18 of primary branch 11 and then exit lumen 18 through distal end 16, then through lumen 52 of luer 50, and ultimately into the patient.

Figure 12D:
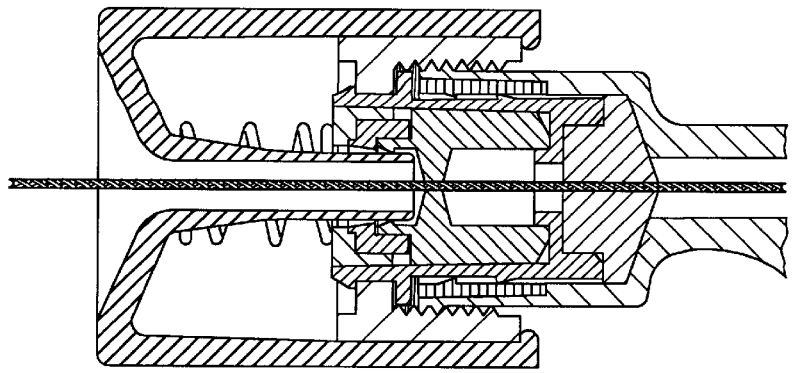
FIGS. 12a to 12d are a cross-sectional view of an operation of a clamp seal clamping a vascular intervention device (such as a catheter) which has been inserted transluminally in a bleed back control assembly in accordance with the present invention.
Figure 12C:
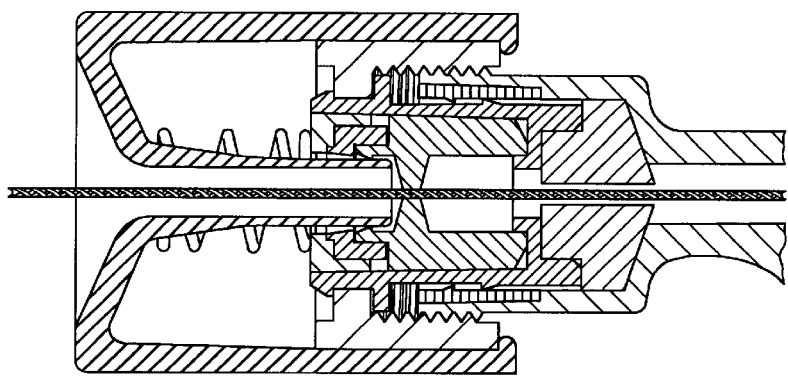
Figure 12B:
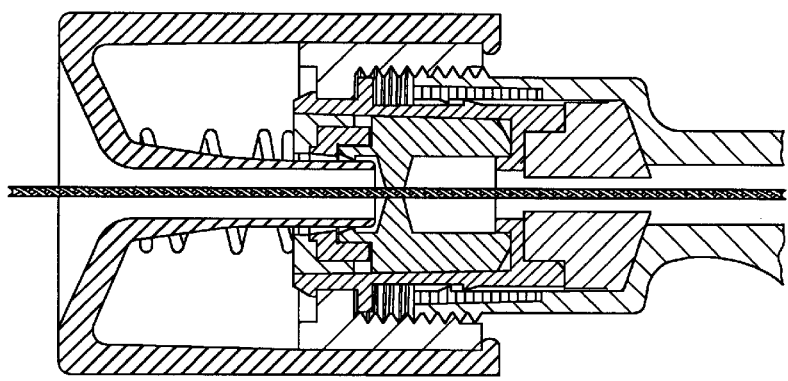
Figure 12A:
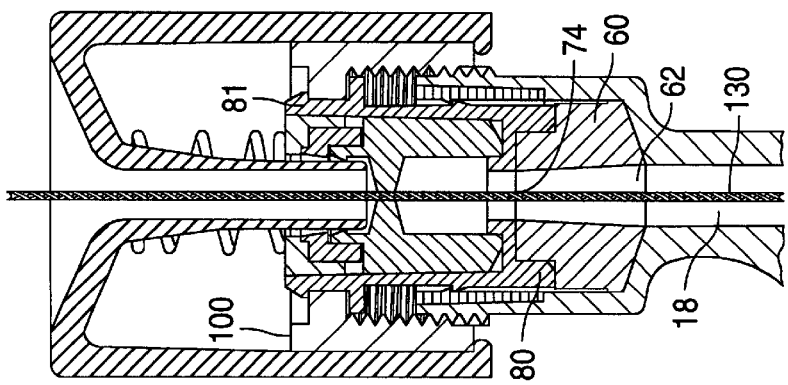

Referring to FIGS. 12a to 12d, clamp seal 60 may also be closed or tightened when a device 130 (such as a catheter) is introduced intratubally within lumen 62 of clamp seal 60. Tightening of threaded cap 100 causes distal movement of seal holder 80 and causes radial and axial compression of clamp seal 60. This compression causes constriction of the diameter of lumen 62 of clamp seal 60, as shown in FIGS. 12b to 12d. As discussed above, a device 130 (such as a catheter) can be introduced through funnel 96 and dilator 92 of funnel cap 90, through aperture 74 of bleed back control seal 70, through aperture 82 of seal holder 80, and through and within lumen 62 of seal clamp 60, and further through aperture 29 and lumen 18 of side arm body 10. If a device 130 has been introduced within lumen 62 of clamp seal 60, then the compression of clamp seal 60 will cause lumen 62 to constrict about the shaft of device 130 within lumen 62. This constriction causes clamp seal 60 to firmly hold or clamp onto device 130. Tightening threaded cap 100 and consequent clamping of clamp seal 60 allows hands free operation for the operator of bleed back control assembly 1.

As noted above, threaded cap 100 may be unscrewed or loosened by rotating threaded cap 100 to cause it to move proximally. This loosening of threaded cap 100 will correspondingly cause seal holder 80 to move proximally as well, since seal holder 80 is connected to threaded cap 100. As discussed above and referring to FIGS. 2 and 3, in one embodiment, seal cavity 14 includes a snap insert 25 which is formed or connected to the interior surface of seal cavity 14. Snap insert 25 includes a blocking notch 27 which extends into seal cavity 14.

Distal to blocking notch 27 there is a corresponding restrictor notch 83 formed on the exterior surface of seal holder 80. The relative spacing between blocking notch 27 and restrictor notch 83 permits threaded cap 100 to be unscrewed a sufficient amount to open clamp seal 60. However, as threaded cap 100 is unscrewed further, restrictor notch 83 of seal holder 80 will impact blocking notch 27, preventing further unscrewing of threaded cap 100. Thus, the restrictive interlocking of blocking notch 27 and restrictor notch 83 will prohibit threaded cap 100 from unscrewing completely from threads 21 of seal cavity 14. The combined effect of blocking notch 27 and restrictor notch 83 ensures that seal body 40 will remain attached to side arm body 10 even when threaded cap 100 is unscrewed as completely as possible.

Operation of Bleed Back Control Seal

As noted above, in one embodiment, seal body 20 may comprise bleed back seal 70, but not include clamp seal 60. In an alternate embodiment, seal body 20 may comprise both clamp seal 60 and bleed back seal 70. In both embodiments, bleed back seal 70 operates to control fluid loss during use of bleed back control assembly 1.

Bleed back control seal 70 is normally closed unless acted upon. The user of bleed back control assembly 1 may open bleed back control seal 70, by dilating aperture or pinhole 74. Because bleed back control seal 70 has an aperture 74 in the center of web area 72, and because the material of bleed back control seal 70 is highly elastic and resilient, stretching of web area 72 will cause aperture 74 to open larger, thus allowing bleed back control seal 70 to open. Because of the elastic and resilient properties of web area 72's material, web area 72 will return to the original, closed position when released after being stretched, thus allowing aperture 74 to close again. Operation of bleed back control seal 70 is discussed with reference to FIGS. 2, 3, 13a to 13d, 14a to 14e, and 15a to 15d.

The user may push or press funnel cap 90 and thus move dilator 92 distally to open or dilate bleed back control seal 70. A user of bleed back control assembly 1 may depress funnel cap 90 axially towards distal end 16 of side arm body 10. This pressing or engaging of funnel cap 90 will also cause dilator 92 to move axially and distally. As shown in FIGS. 13a to 13d, when funnel cap 90 is pushed, dilator 92 will abut web area 72 of bleed back control seal 70.

Figure 13D:
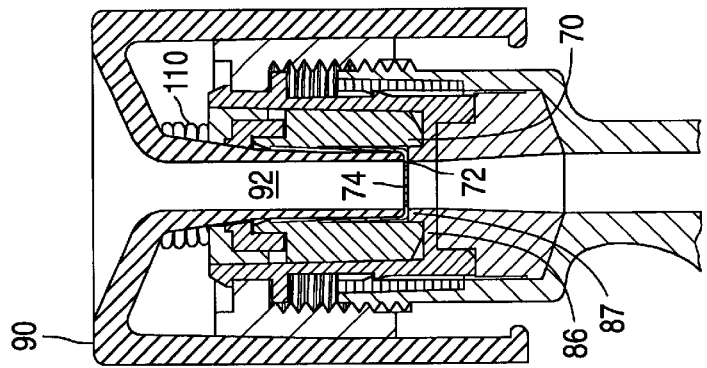
FIGS. 13a to 13d are a cross-sectional view of an operation of a funnel cap and dilator in relation to a bleed back control seal in accordance with the present invention.
Figure 13C:
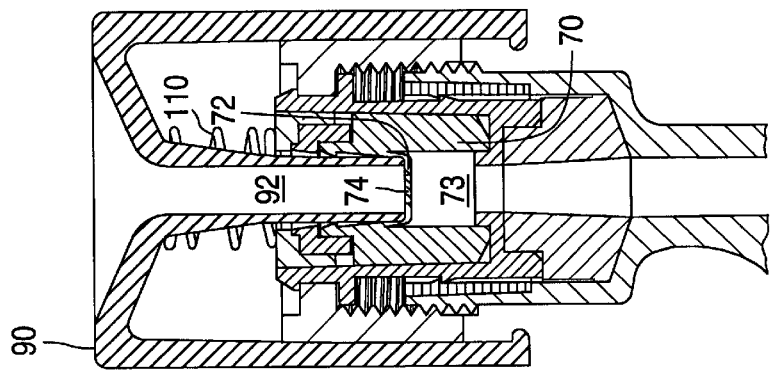
Figure 13B:
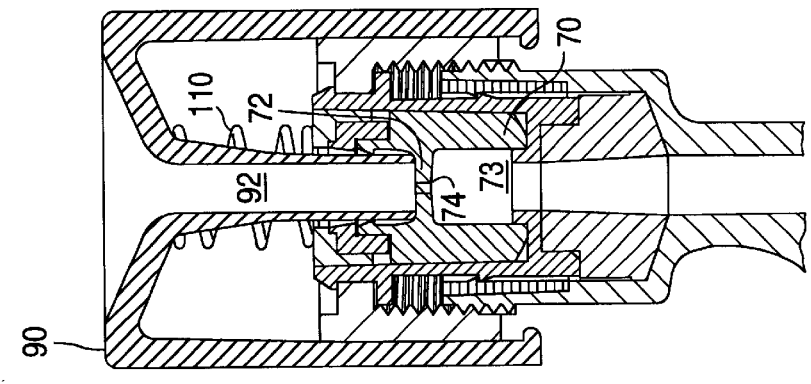
Figure 13A:
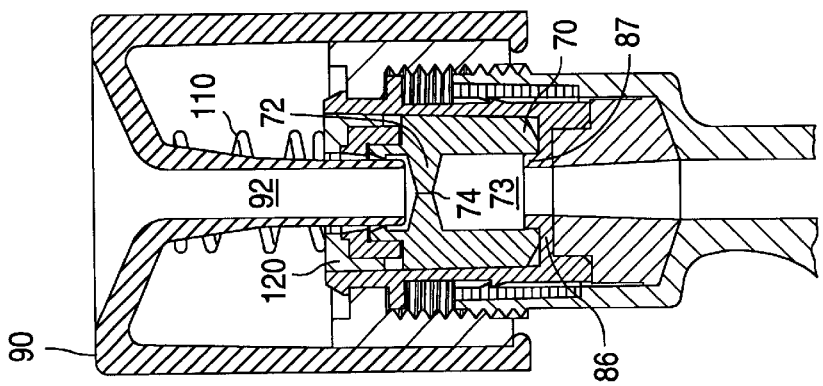
Figures 14A, 14B, 14C, 14D, 14E:
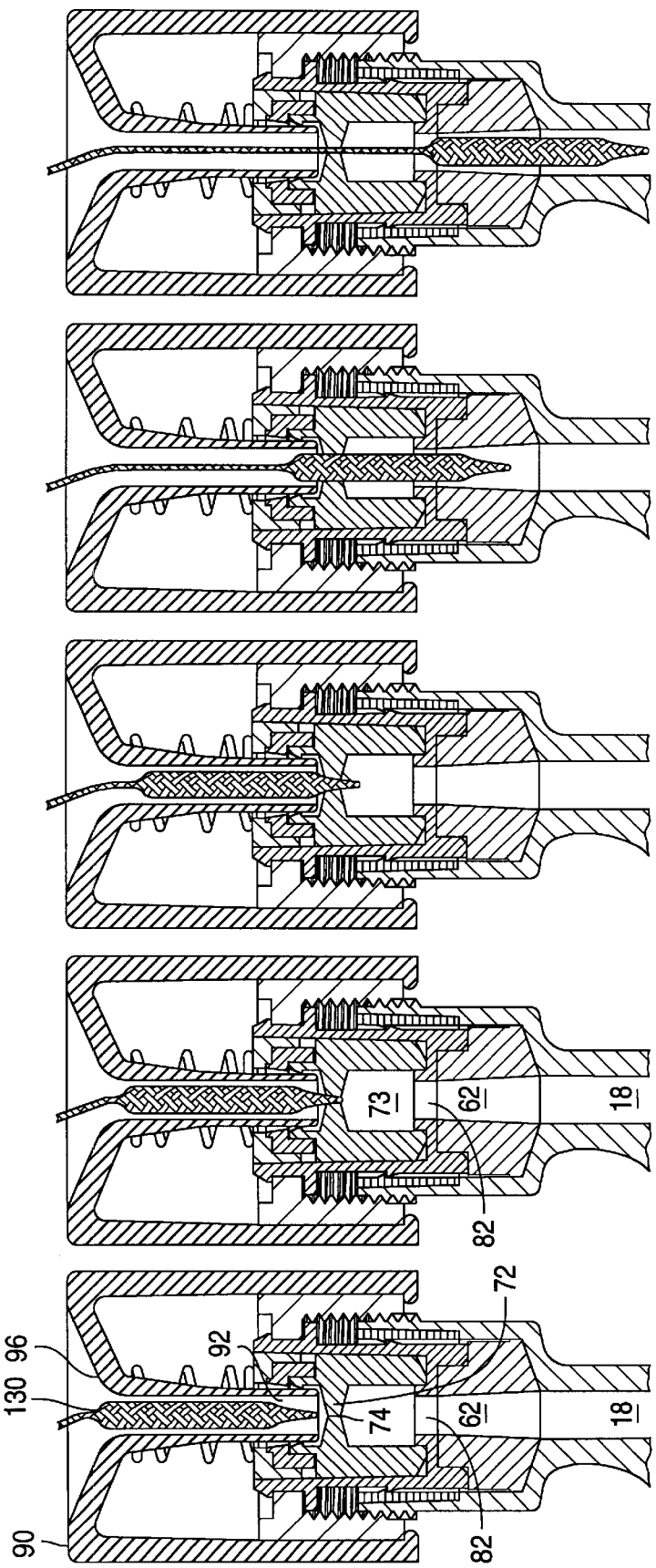
FIGS. 14a to 14e are a cross-sectional view of an insertion of a vascular intervention device (such as a catheter) through a bleed back control seal in accordance with the present invention.

Axial movement of funnel cap 90 and dilator 92 causes bleed back control seal 70 to open by stretching the material of web area 72 distally. Web area 72 will be stretched and pushed into chamber 73 of bleed back control seal 70. This stretching of web area 72 will cause aperture 74 to open wider or dilate. Pushing funnel cap 90 also causes spring 110 to constrict or compress. As shown in FIG. 13d, dilator 92 may be moved distally until dilator 92 is blocked by impact with risers 87 and distal legs 86 of seal holder 80.

Referring to FIGS. 13a to 13d, the diameter of bottom chamber 73 formed by side arms 76 of bleed back control seal 70 is larger than the diameter of dilator 92. This difference in diameters provides a break away for the material of web area 72 as web area 72 is pushed and stretched into bottom chamber 73 as dilator 92 moves distally.

Return spring 110, wound around the exterior of dilator 92 and inside chamber 94 of funnel cap 90, causes funnel cap 90 to return to the starting, original position when the user releases or stops pushing funnel cap 90. The decompressing action of spring 110 moves dilator 92 proximally, thus allowing bleed back control seal 70 to return to its original shape and close aperture 74 again. Removal of dilator 92 away from web area 72 of bleed back control seal 70 causes bleed back control seal 70 to close by allowing the resilient material of web area 72 to return to its original shape and position. As the elastic material of web area 72 contracts back to its original shape, aperture 74 will correspondingly grow smaller, until eventually aperture 74 formed in web area 72 of bleed back control seal 70 will close.

In one embodiment, threaded cap 100 does not cause dilation or opening of bleed back control seal 70. Threaded cap 100 may be operated as discussed above to rotate and thus cause seal holder 80 to move axially. As noted above, threaded cap 100 has interior arms 101 which abut or engage the proximal end 78 of bleed back control seal 70. Thus, tightening of threaded cap 100 causes corresponding movement axially of seal holder 80 and bleed back control seal 70 without causing dilation of aperture 74 of web area 72.

In an alternate embodiment, dilator 92 may be attached to threaded cap 100 (as opposed to funnel cap 90), and in this embodiment rotation or adjustment of threaded cap 100 will cause dilator 92 to impact and open aperture 74 of web area 72 of bleed back control seal 70. Thus, in this embodiment, threaded cap 100 is operated by the user to open and close bleed back control seal 70.

During use of bleed back control assembly 1, a user may decide to introduce a device 130 (such as a catheter or guidewire) into the bleed back control assembly 1. Referring to FIGS. 14a to 14e, the user may insert a device 130 into funnel surface 96 of funnel cap 90. Device 130 then continues into the lumen of dilator 92. Device 130 then moves through aperture 74 of bleed back control seal 70. (The user may decide to dilate or not dilate aperture 74 depending on the user's desires or the size of device 130). Device 130 then continues through aperture 82 in the bottom of seal holder 80, and thence into lumen 62 of clamp seal 60. Then, device 130 will enter lumen 18 of side arm body 10. Continued insertion will cause device 130 to move through lumen 18, through lumen 52 in luer connector 50, and ultimately into the patient's body in any suitable or desired location and structure, either transluminally, transvenously, or in any other appropriate diagnostic or interventional manner.

Dilation of bleed back control seal 70 is not necessary for insertion of many devices 130, such as catheters and guidewires. Referring to FIGS. 15a to 15d, a user has the option to dilate aperture 74 of bleed back control seal 70 before inserting a device 130 through aperture 74. In order to introduce a larger device 130 such as a stent with associated delivery system, a user may engage funnel cap 90 and dilator 92, push them axially and distally, and thereby open or dilate aperture 74 of bleed back control seal 70 to allow greater ease of insertion of device 130.

An operator of bleed back control assembly 1 may thus introduce a guidewire, catheter, or other desired device 130 through funnel cap 90 into dilator 92, through dilated aperture 74 of bleed back control seal 70, through bottom chamber 73 of bleed back control seal 70, through aperture 82 of seal holder 80, through lumen 62 of clamp seal 60, then into primary lumen 18 of side arm body 10, and ultimately into the patient.

A device 130 may be removed by withdrawing device 130 back through these same structures in reverse order. Both during insertion and withdrawal, the user may choose to dilate or stop dilating aperture 74 of bleed back control seal 70, at any time.

One of ordinary skill would understand that device 130 may be any appropriate transluminal or interventional device. For example, device 130 may be a catheter, stent, guidewire, balloon catheter, or any other suitable device. A user desiring to introduce a stent into bleed back control assembly 1 may introduce the stent without necessarily requiring use of dilator 92 to open aperture 74 of bleed back control seal 70. Guidewires may be introduced into bleed back control assembly 1 with an introducer and, if an introducer is used, then bleed back control seal 70's aperture 74 does not need to be opened with dilator 92. A balloon catheter may also be introduced into bleed back control assembly 1 without necessarily dilating bleed back control seal 70.

Because of the elastic and resilient material properties of bleed back control seal 70, bleed back control seal 70's web area 72 is self sizing around device 130 introduced through aperture 74. Bleed back control seal 70 thus inhibits the loss of blood or other fluids when a user has inserted a device 130 through aperture 74 of bleed back control seal 70. Bleed back control seal 70 thus controls fluid or blood loss both with and without devices 130 intratubal. A device 130 penetrating bleed back control seal 70 can be moved into and out of side arm body 10 with substantially low fluid leakage and resistance.

A user may manipulate funnel cap 90 (and thus dilator 92) to open bleed back control seal 70 and allow the purging of gases or undesired fluids from the interior of bleed back control assembly 1. A user may push or press funnel cap 90 and dilator 92 to cause aperture 74 to open, and this will allow the pressure of fluids within bleed back control assembly 1 to purge gases or fluids trapped inside assembly 1, by causing the gases or fluids to exit dilator 92 and out through the proximal end of assembly 1.

As noted above, bleed back control seal 70 in the closed position can withstand pressures of at least approximately 40–100 psi without leaking. As noted above, if an alternate embodiment of web area 72 and aperture 74 is used, as in FIG. 5c, then bleed back control seal 70 in the closed position can withstand pressures of approximately 500 psi. As noted above, an alternate embodiment for bleed back control seal 70 may include spherical portion 79 as shown in FIG. 5d. In this embodiment, bleed back control seal 70 in the closed position may withstand pressures of approximately 400 psi. Therefore, even when clamp seal 60 is in the open position, bleed back control seal 70 (which is normally closed) can prevent leakage of fluid out of the proximal end of bleed back control assembly 1. This may be advantageous, for example, when the user performs injections through secondary branch 13 of the side arm body 10 at appropriate pressures while clamp seal 60 is open.

Accordingly, bleed back control assembly 1 of the present invention provides blood loss control during insertion, movement, and removal of devices 130 from assembly 1. Assembly 1 can be adjusted to clamp an intratubal device 130 to maintain device position.

Moreover, closure of clamp seal 60 with or without a device 130 intratubal to assembly 1 allows the user to introduce high pressure injections through lumen 15 of secondary branch 13 of the side arm body 10.

Other Embodiments

While several aspects of the invention have been described with regard to specific embodiments, those skilled in the art will recognize that changes can be made in form and detail without departing from the spirit and scope of the invention.

In one embodiment, the approximate dimensions of some of the components of side arm body 10 and seal body 40 may be approximately as follows:

| COMPONENT | DIMENSIONS (in inches, ±0.005) |
| --- | --- |
| Side arm body 10 | Overall length: 1.82 |
| | Length of secondary branch 13: 1.15 |
| | Length of seal cavity 14: 0.46 |
| | Interior diameter of seal cavity 14: 0.38 |
| | Diameter of primary lumen 18: 0.12 |
| | Diameter of secondary lumen 15: 0.17 |
| Clamp seal 60 | Length: 0.26 |
| | Max. diameter of frustum portion 61: 0.39 |
| | Length of frustum portion 61: 0.05 |
| | Length of cylinder portion 63: 0.03 |
| | Length of cylinder portion 65: 0.10 |
| | Length of cylinder portion 67: 0.08 |
| | Width of cylinder portion 63: 0.39 |
| | Width of cylinder portion 65: 0.37 |
| | Width of cylinder portion 67: 0.27 |
| | Diameter of top aperture of lumen 62: 0.1 |
| | Diameter of bottom aperture of lumen 62: 0.12 |
| Bleed back control seal 70 | Length: 0.35 |
| | Maximum width: 0.31 |
| | Diameter of top lumen 75: 0.14 |
| | Diameter of bottom lumen 73: 0.16 |

-continued

| COMPONENT | DIMENSIONS (in inches, ±0.005) |
|---|---|
| Seal holder 80 | Length: 0.54 |
| | Diameter of top chamber 88: 0.29 |
| | Diameter of bottom chamber 85: 0.25 |
| | Length of top chamber 88: 0.43 |
| | Length of bottom chamber 85: 0.08 |
| | Length of aperture 82: 0.06 |
| | Diameter of aperture 82: 0.10 |
| Funnel cap 90 | Length: 0.90 |
| | Exterior diameter: 0.71 |
| | Diameter of interior chamber 94: 0.60 |
| | Length of dilator 92: 0.46 |
| | Diameter of lumen of dilator 92: 0.98 |
| Threaded cap 100 | Length: 0.36 |
| | Diameter: 0.59 |
| | Proximal diameter of center hole 102: 0.15 |
| | Distal diameter of center hole 102: 0.19 |

Those of ordinary skill will appreciate that the various components and sub-assemblies described with respect to alternate embodiments may be rearranged or combined with each other without departing from the scope of the invention. For example, components of cap assembly 30 may be incorporated as part of seal assembly 20, and vice versa. As noted above, seal body 20 may not include clamp seal 60 in one embodiment. Also, structures of threaded cap 100 may be incorporated in funnel cap 90, and vice versa.

Alternate embodiments also include adding a position lock for engaging and disengaging funnel cap 90 and dilator 92 (analogous to the manner by which a conventional ball point pen is depressed), thus requiring a user to engage or depress funnel cap 90 axially in order to engage and disengage dilator 92 from opening bleed back control seal 70.

Alternatively, funnel cap 90 and dilator 92 may be locked or unlocked in the open or closed positions with a bayonet style lock, where the lock mode would allow the operator to lock dilator 92 in either the open or closed position to either dilate or not dilate aperture 74 of bleed back control seal 70, whichever is desired.

Other embodiments include using a locking mechanism, such as a detent, using a twist motion of funnel cap 90 (of any suitable predetermined amount of rotation) for locking dilator 92 in the open or closed positions.

In another embodiment, side arm body 10 comprises primary branch 11 and does not include secondary branch 13. In this embodiment, finger rest 19 may be formed on the exterior surface of primary branch 11 of side arm body 10.

In another embodiment, there may be a plurality of secondary branches 13 in addition to primary branch 11 of side arm body 10. In this embodiment, none, some, or all of these plurality of secondary branches 13 may have their own finger rest 19 formed thereon, in addition to or in substitution for a finger rest 19 formed on the exterior surface of primary branch 11.

In another embodiment, side arm body 10, snap insert 25, luer connector 50, seal holder 80, funnel cap 90, threaded cap 100, spring 110, and snap retainer 120 may each be formed of other appropriate rigid materials or composite materials, such as metal, metallic alloys, other resins, different plastics, glass, or any suitable composite.

In another embodiment, device 130 may be any device appropriate for inserting into any part of a patient's body, such as insertion into a blood vessel or any other luminal structure or any body cavity. For example, device 130 may be any type of catheter, guidewire, stent, balloon catheter, perfusion balloon, guiding catheter, rapid exchange catheter, over-the-wire balloon, directional coronary atherectomy catheter, or other appropriate device.

Persons of ordinary skill will appreciate that changes can be made to dimensions, sizing, relative dimensions, materials, spatial and angular relationships of and between components, and manufacturing processes and other commercial or industrial techniques, all without departing from the scope of the invention.

We claim:

1. A bleed back control assembly comprising:

a side arm body having a proximal end, a distal end, and a lumen connecting said proximal and distal ends, said side arm body also having a seal cavity formed in said proximal end, said lumen being in fluid communication with said seal cavity;

a seal mechanism coupled to the proximal end of said side arm body, said seal mechanism comprising:

a cap assembly coupled to a seal assembly and coupled to said proximal end of said side arm body, said cap assembly restraining said seal assembly within said seal cavity and said cap assembly operable to engage said seal assembly in response to active user manipulation and disengage from said seal assembly in the absence of active user manipulation and said cap assembly having a lumen having a proximal aperture communicating with the exterior of said cap assembly; and said seal assembly comprising elastomeric material inhibiting said cap assembly lumen from being in fluid communication with said side arm body lumen; and wherein said cap assembly is operable to control axial translation and displacement of said seal mechanism; and wherein displacement of said cap assembly is limited by one or more stop means, wherein said stop means comprises one or more notches formed in the interior of said cap assembly.

2. A bleed back control assembly comprising:

a side arm body having a proximal end, a distal end, and a lumen connecting said proximal and distal ends, said side arm body also having a seal cavity formed in said proximal end, said lumen being in fluid communication with said seal cavity;

a seal mechanism coupled to the proximal end of said side arm body, said seal mechanism comprising:

a cap assembly coupled to a seal assembly and coupled to said proximal end of said side arm body, said cap assembly restraining said seal assembly within said seal cavity and said cap assembly operable to engage said seal assembly in response to active user manipulation and disengage from said seal assembly in the absence of active user manipulation and said cap assembly having a lumen having a proximal aperture communicating with the exterior of said cap assembly; and said seal assembly comprising elastomeric material inhibiting said cap assembly lumen from being in fluid communication with said side arm body lumen; and wherein said seal cavity has an interior distal surface including an aperture allowing fluid communication between said side arm body lumen and said seal cavity, said seal assembly comprising:

a seal holder which is movable axially, said seal holder distal to said lumen aperture and having an interior chamber; and a bleed back control seal held within said interior chamber of said seal holder, said bleed back control seal having an aperture which is closed unless acted upon for controlling blood loss during operation of said assembly; and further wherein said cap assembly comprises a dilator, said dilator operable to be forcibly introduced through said aperture of said bleed back control seal.

3. A bleed back control assembly comprising:

a side arm body having a proximal end, a distal end, and a lumen connecting said proximal and distal ends, said side arm body also having a seal cavity formed in said proximal end, said lumen being in fluid communication with said seal cavity;

a seal mechanism coupled to the proximal end of said side arm body, said seal mechanism comprising:
  a cap assembly coupled to a seal assembly and coupled to said proximal end of said side arm body, said cap assembly restraining said seal assembly within said seal cavity and said cap assembly operable to engage said seal assembly in response to active user manipulation and disengage from said seal assembly in the absence of active user manipulation and said cap assembly having a lumen having a proximal aperture communicating with the exterior of said cap assembly; and
  said seal assembly comprising elastomeric material inhibiting said cap assembly lumen from being in fluid communication with said side arm body lumen; and wherein said seal cavity has an interior distal surface including an aperture allowing fluid communication between said side arm body lumen and said seal cavity, said seal assembly comprising:
  a seal holder which is movable axially, said seal holder distal to said lumen aperture and having an interior chamber; and
  a bleed back control seal held within said interior chamber of said seal holder, said bleed back control seal having an aperture which is closed unless acted upon for controlling blood loss during operation of said assembly; and
  wherein said cap assembly comprises: a dilator and a spring wound around said dilator, said spring pushing unidirectionally.

4. A bleed back control assembly comprising:

a side arm body having a proximal end, a distal end, and a lumen connecting said proximal and distal ends, said side arm body also having a seal cavity formed in said proximal end, said lumen being in fluid communication with said seal cavity;

a seal mechanism coupled to the proximal end of said side arm body, said seal mechanism comprising:
  a cap assembly coupled to a seal assembly and coupled to said proximal end of said side arm body, said cap assembly restraining said seal assembly within said seal cavity and said cap assembly operable to engage said seal assembly in response to active user manipulation and disengage from said seal assembly in the absence of active user manipulation and said cap assembly having a lumen having a proximal aperture communicating with the exterior of said cap assembly; and said seal assembly comprising elastomeric material inhibiting said cap assembly lumen from being in fluid communication with said side arm body lumen; and wherein said seal cavity has an interior distal surface including an aperture allowing fluid communication between said side arm body lumen and said seal cavity, said seal assembly comprising:
  a seal holder which is movable axially, said seal holder distal to said lumen aperture and having an interior chamber; and
  a bleed back control seal held within said interior chamber of said seal holder, said bleed back control seal having an aperture which is closed unless acted upon for controlling blood loss during operation of said assembly, wherein said bleed back control seal is movable axially in response to user manipulation of said cap assembly.

5. A bleed back control assembly comprising:

a side arm body having a proximal end, a distal end, and a lumen connecting said proximal and distal ends, said side arm body also having a seal cavity formed in said proximal end, said lumen being in fluid communication with said seal cavity;

a seal mechanism coupled to the proximal end of said side arm body, said seal mechanism comprising:
  a cap assembly coupled to a seal assembly and coupled to said proximal end of said side arm body, said cap assembly restraining said seal assembly within said seal cavity and said cap assembly operable to engage said seal assembly in response to active user manipulation and disengage from said seal assembly in the absence of active user manipulation and said cap assembly having a lumen having a proximal aperture communicating with the exterior of said cap assembly; and said seal assembly comprising elastomeric material inhibiting said cap assembly lumen from being in fluid communication with said side arm body lumen; and wherein said seal cavity has an interior distal surface including an aperture allowing fluid communication between said side arm body lumen and said seal cavity, said seal assembly comprising:
  a seal holder which is movable axially, said seal holder distal to said lumen aperture and having an interior chamber; and
  a bleed back control seal held within said interior chamber of said seal holder, said bleed back control seal having an aperture which is closed unless acted upon for controlling blood loss during operation of said assembly, and wherein said bleed back control seal comprises a valve which is operable to be closed when in a resting idle position and open when in an active working position, whereby opening of said valve allows passage of an interventional device into the lumen of said bleed back control assembly.

* * * * *

UNITED STATES PATENT AND TRADEMARK OFFICE
CERTIFICATE OF CORRECTION

PATENT NO. : 6,331,176 B1
DATED : December 18, 2001
INVENTOR(S) : Neil M. Becker et al.

It is certified that error appears in the above-identified patent and that said Letters Patent is hereby corrected as shown below:

<u>Title page,</u>
Item [75], under "Inventors", add -- LaShun D. Tarver --.

Signed and Sealed this

Twenty-seventh Day of August, 2002

Attest:

JAMES E. ROGAN
Attesting Officer          Director of the United States Patent and Trademark Office